(12) United States Patent
Lo et al.

(10) Patent No.: US 7,829,285 B2
(45) Date of Patent: Nov. 9, 2010

(54) CIRCULATING MRNA AS DIAGNOSTIC MARKERS

(75) Inventors: Yuk-Ming Dennis Lo, Kowloon (HK); Kai On Ng, New Territories (HK); Bo Yin Tsui, Kowloon (HK); Wai Kwun Rossa Chiu, New Territories (HK)

(73) Assignee: The Chinese University of Hong Kong, Shatin, New Territories, SAR (HK)

( * ) Notice: Subject to any disclaimer, the term of this patent is extended or adjusted under 35 U.S.C. 154(b) by 300 days.

(21) Appl. No.: 11/807,258

(22) Filed: May 24, 2007

(65) Prior Publication Data

US 2009/0162842 A1 Jun. 25, 2009

Related U.S. Application Data

(62) Division of application No. 10/759,783, filed on Jan. 16, 2004, now Pat. No. 7,235,359.

(60) Provisional application No. 60/440,906, filed on Jan. 17, 2003.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.1; 435/91.2; 435/91.21; 536/23.5; 436/65

(58) Field of Classification Search ...................... None
See application file for complete search history.

(56) References Cited

U.S. PATENT DOCUMENTS

| 5,750,339 | A | 5/1998 | Smith |
| 6,258,540 | B1 | 7/2001 | Lo et al. |
| 6,635,452 | B1 | 10/2003 | Monforte et al. |
| 6,664,056 | B2 | 12/2003 | Lo et al. |
| 2002/0045176 | A1 | 4/2002 | Lo et al. |

FOREIGN PATENT DOCUMENTS

| CA | 2460803 | * | 4/2003 |
| WO | 02/04678 | A2 | 1/2002 |
| WO | 02/103352 | A1 | 12/2002 |
| WO | 03/095674 | A2 | 11/2003 |

OTHER PUBLICATIONS

Lee et al. Journal of the National Cancer Institute. 1996. 88: 1731-1737.*
Janneau et al. The Journal of clinical Endocrinology & Metabolism. 2002. 87: 5336-5339.*
Amicucci, Paola et al.; "Prenatal Diagnosis of Myotonic Dystrophy Using Fetal DNA Obtained from Maternal Plasma"; 2000, *Clinical Chemistry* vol. 46, No. 2, pp. 301-302.
Braun, Siegmund L. et al.; "Plasma Troponin T and Troponin I after Minimally Invasive Coronary Bypass Surgery"; 2000. *Clinical Chemistry* vol. 46, No. 2, pp. 279-301.
Chiu, Rossa W.K. et al.; "Prenatal exclusion of β thalassaemia major by examination of material plasma"; 2002, *The Lancet* vol. 360, pp. 998-1000.
Inder, et al., "The Utility of Plasma CRH as a Predictor of Preterm Delivery;" 2001; *The Journal of Clinical Endocrinology & Metabolism*; vol. 86; pp. 5706-5710.
Johansen, Marianne et al.; "An Investigation of Methods for Enriching Trophoblast from Maternal Blod"; 1995 *Prenat. Diagn.*, vol. 15, pp. 921-931.
Lo, Dennis Y.M. et al.; "Prenatal sex determination from maternal peripheral blood using the polymerase chain reaction"; 1993 *Hum. Genet.*, vol. 90, pp. 483-488.
Lo, Dennis Y.M. et al.; "Presence of fetal DNA in maternal plasma and serum"; 1997, *The Lancet*, vol. 350, pp. 485-487.
Lo, Dennis Y.M. et al.; "Prenatal Diagnosis of Fetal RhD Status by Molecular Analysis of Maternal Plasma"; 1998, *The New England Journal of Medicine*, vol. 339, No. 24, pp. 1734-1738.
Lo, Dennis Y.M. et al.; "Quantitative Abnormalities of Fetal DNA in Maternal Serum in Preeclampsia"; 1999 *Clinical Chemistry*, vol. 45, No. 2, pp. 184-188.
Lo, Dennis Y.M. et al.; "Increased Fetal DNA Concentrations in the Plasma of Pregnant Women Carrying Fetuses with Trisomy 21"; 1999, *Clinical Chemistry*, vol. 45, No. 10, pp. 1747-1751.
Lo, Kwok-Wai et al.; "Analysis of Cell-free Epstein-Barr Virus-associated RNA in the Plasma of Patients with Nasopharyngeal Carcinoma"; 1999, *Clinical Chemistry*, vol. 45, No. 8, pp. 1292-1294.
Ng, Enders K.O. et al.; "mRNA of placental origin is readily detectable in maternal plasma"; 2003, *PNAS*, vol. 100, No. 8, pp. 4748-4753.
Ng, Enders K.O. et al.; "Presence of Filterable and Nonfilterable mRNA in the Plasma of Cancer Patients and Healthy Individuals"; 2002, *Clinical Chemistry*, vol. 48, No. 8, pp. 1212-1217.
Ng, Enders K.O. et al.; "The Concentration of Circulating Corticotropin-releasing Hormone mRNA in Maternal Plasma is Increased in Preeclampsia"; 2003, *Clinical Chemistry*, vol. 49, No. 5, pp. 727-731.
Poon, Leo L.M. et al.; "Presence of Fetal RNA in Maternal Plasma"; 2000, *Clinical Chemistry*, vol. 46, No. 11, pp. 1832-1833.
Sekizawa, Akihiko et al.; "Cell-free Fetal DNA is Increased in Plasma of Women with Hyperemesis Gravidarum"; 2001, *Clinical Chemistry*, vol. 47, No. 12, pp. 2164-2165.
Saito, Hiroshi et al.; "Prenatal DNA diagnosis of a single-gene disorder from maternal plasma"; 2000, *The Lancet*, vol. 356, pp. 1170.
Silva, J.M. et al.; "Detection of epithelial tumour RNA in the plasma of colon cancer patients is associated with advanced stages and circulating tumour cells"; 2002, *Gut*, vol. 50, pp. 530-534.

(Continued)

*Primary Examiner*—Carla Myers
(74) *Attorney, Agent, or Firm*—Townsend and Townsend and Crew LLP

(57) ABSTRACT

Methods and kits are provided for diagnosing, monitoring, or predicting the conditions of pre-eclampsia, fetal chromosomal aneuploidy, and pre-term labor in a pregnant woman, as well as for detecting pregnancy in a woman, by quantitatively measuring in the maternal blood the amount of one or more mRNA species encoding human chorionic gonadotropin β subunit (hCG-β), human placental lactogen (hPL), human corticotropin releasing hormone (hCRH), KiSS-1 metastasis-suppressor (KISS1), tissue factor pathway inhibitor 2 (TPFI2), placenta-specific 1 (PLAC1), or glyceraldehyde-3-phosphate dehydrogenase (GAPDH), and comparing the amount of the mRNA species with a standard control.

8 Claims, 10 Drawing Sheets

OTHER PUBLICATIONS

Zhong, Xiao Yan et al.; "Fetal DNA in maternal plasma is elevated in pregnancies with aneuploid fetuses"; 2000, *Prenatal Diagnosis*, vol. 20, pp. 795-798.

Zhong, Xiao Yan et al.; "Elevation of both maternal and fetal extracellular circulating deoxyribonucleic acid concentrations in the plasma of pregnant women with preeclampsia"; 2001 *Am. J. Obstet Gynecol*, vol. 184, No. 3, pp. 414-419.

Brizot, Marie L. et al.; "Placental mRNA expression of α and β human chorionic gonadotrophin in early trisomy 18 pregnancies", 1996, *Molecular Human Reproduction*, vol. 2, No. 6, pp. 463-465.

Chen, Ellson Y. et al.; "The Human Growth Hormone Locus: Nucleotide Sequence, Biology, and Evolution"; 1989, *Genomics*, vol. 4, No. 4, pp. 479-497.

Fant, Michael et al.; "PLAC1, a trophoblast-specific gene, is expressed throughout pregnancy in the human placenta and modulated by keratinocyte growth factor"; (abstract) 2002, *Molecular Reproduction and Development*, vol. 63, No. 4, pp. 430-436.

Poon, Leo L.M. et al.; "Circulating Fetal RNA in Maternal Plasma"; 2001, *Antisense Strategies*, vol. 945, pp. 207-210.

Yagel, Simcha et al.; "Trophoblasts circulating in matgernal blood as candidates for prenatal genetic evaluation"; 1994, *Human Reproduction*, vol. 9, No. 6, pp. 1184-1189.

* cited by examiner

A

B

C

D

CIRCULATING MRNA AS DIAGNOSTIC MARKERS

CROSS REFERENCE TO RELATED APPLICATIONS

This application is a divisional of U.S. application Ser. No. 10/759,783, filed Jan. 16, 2004, now U.S. Pat. No. 7,235,359 which claims priority to U.S. Provisional Application No. 60/440,906, filed Jan. 17, 2003, the contents of both are incorporated herein by reference in their entirety.

BACKGROUND OF THE INVENTION

Prenatal diagnosis has been routinely conducted using cells isolated from the fetus through procedures such as chorionic villus sampling (CVS) or amniocentesis. These conventional methods are, however, invasive and present an appreciable risk to both the mother and the fetus despite most careful handling (Tabor et al., Lancet 1:1287-1293, 1986).

Alternatives to these invasive approaches have been developed for prenatal screening, e.g., to detecting fetal abnormalities, following the discoveries that several types of fetal cells can be found in maternal circulation (Johansen et al., Prenat. Diagn. 15:921-931, 1995) and more importantly, circulating cell-free fetal DNA can be detected in maternal plasma and serum (Lo et al., Lancet 350:485-487, 1997). The amount of fetal DNA in maternal blood has been shown to be sufficient for genetic analysis without complex treatment of the plasma or serum, in contrast to the necessary steps for isolating and enriching fetal cells. Fetal rhesus D (RhD) genotyping (Lo et al., N. Engl. J. Med. 339:1734-1738, 1998), fetal sex determination (Lo et al., Hum. Genet. 90:483-488, 1993), and diagnosis of several fetal disorders (Amicucci et al., Clin. Chem. 46:301-302, 2000; Saito et al., Lancet 356:1170, 2000; and Chiu et al., Lancet 360:998-1000, 2002) have since been achieved by detecting fetal DNA in maternal blood using a polymerase chain reaction (PCR)-based technique.

In addition, quantitative abnormalities of fetal DNA in maternal plasma/serum have also been reported in preeclampsia (Lo et al., Clin. Chem. 45:184-188, 1999 and Zhong et al., Am. J. Obstet. Gynecol. 184:414-419, 2001), fetal trisomy 21 (Lo et al., Clin. Chem. 45:1747-1751, 1999 and Zhong et al. Prenat. Diagn. 20:795-798, 2000) and hyperemesis gravidarum (Sekizawa et al., Clin. Chem. 47:2164-2165, 2001). Detection of fetal nucleic acid in maternal blood for prenatal genetic analysis is also disclosed in U.S. Pat. No. 6,258,540.

When analyzing fetal DNA, investigators have often used Y chromosomal markers, which are only present in male fetuses, as a fetal-specific marker. This approach has limited the application of this technology to the 50% of pregnant women who are carrying male fetuses. Further, the use of other genetic polymorphisms has also increased the complexity of fetal DNA-based analyses. The discovery of fetal RNA in maternal plasma offers a possible new approach that circumvents these limitations (Poon et al., Clin. Chem. 46:1832-1834, 2000).

More recently, U.S. patent application Ser. No. 09/876,005 discloses non-invasive techniques based on detection of fetal RNA in maternal blood. The present invention discloses for the first time that the amount of certain mRNA species present in maternal blood, including those encoding human chorionic gonadotropin β subunit (hCG-β), human corticotropin releasing hormone (hCRH), human placental lactogen (hPL), KiSS-1 metastasis-suppressor (KISS1), tissue factor pathway inhibitor 2 (TPFI2), placenta-specific 1 (PLAC1), or glyceraldehyde-3-phosphate dehydrogenase (GAPDH), can be used as markers for diagnosing, monitoring, or predicting pregnancy-related disorders such as preeclampsia, fetal chromosomal aneuploidy, and pre-term labor, as well as for detecting pregnancy.

BRIEF SUMMARY OF THE INVENTION

The present invention provides new methods for diagnosing, monitoring, or predicting pregnancy-related disorders such as preeclampsia, fetal chromosomal aneuploidy, and pre-term labor by measuring the amount of one or more species of circulating mRNA found in the maternal blood. Methods for detecting pregnancy in a woman are also provided based on the same methodology. The mRNA may encode proteins of fetal or maternal origin such as human chorionic gonadotropin β subunit (hCG-β), human placental lactogen (hPL), human corticotropin releasing hormone (hCRH), KiSS-1 metastasis-suppressor (KISS1), tissue factor pathway inhibitor 2 (TPFI2), placenta-specific 1 (PLAC1), and glyceraldehyde-3-phosphate dehydrogenase (GAPDH). Diagnostic/detection kits for these pregnancy-related conditions/pregnancy based on the invention are also provided.

One aspect of the present invention relates to a method for diagnosing, monitoring, or predicting preeclampsia in a pregnant woman. This method comprises multiple steps: the first step is to quantitatively determine the amount of one or more particular species of mRNA present in the pregnant woman's blood. The mRNA may encode hCG-β, hCRH, hPL, KISS1, TPFI2, PLAC1, or GAPDH. The second step is to compare the amount of mRNA obtained from the first step to a standard control representing the amount of mRNA encoding the same protein(s) in the blood of an average non-preeclamptic woman. An increase or a decrease in the mRNA level indicates either the presence of preeclampsia or an increased risk of developing the condition.

In some embodiments, the mRNA used as marker in this method encodes hCRH or GAPDH. In some embodiments, the first step of the method is performed by reverse transcription polymerase chain reaction (RT-PCR), whereas in others this first step is carried out using a polynucleotide hybridization method or mass spectrometry. In some embodiments, the pregnant woman is during the first trimester of gestation, whereas in others the woman is during the second or third trimester of gestation. In some embodiments, the pregnant woman's blood is rendered acellular before it is used in the first step of the method. In some embodiments, plasma or serum is used in the first step of the method. In some embodiments, the increase in the amount of mRNA from the standard control is more than 2-fold.

The method of the present invention may also be used for diagnosis, monitoring, or prediction of a more severe clinical course than preeclampsia, such as eclampsia.

The invention also relates to a kit for diagnosing, monitoring, or predicting preeclampsia in a pregnant woman. The kit comprises PCR primers for quantitatively determining the amount of one or more particular species of mRNA in the pregnant woman's blood. The mRNA may encode hCG-β, hCRH, hPL, KISS1, TPFI2, PLAC1, or GAPDH. The kit further comprises a standard control that represents the amount of mRNA encoding the same protein(s) in an average non-preeclamptic pregnant woman. A kit of the present invention may, in addition to or in place of the PCR primers, comprise one or more probes that can be used to quantitatively determine the amount of mRNA encoding hCG-β, hCRH, hPL, KISS1, TPFI2, PLAC1, or GAPDH.

Another aspect of the present invention relates to a method for detecting the presence of a fetus with a chromosomal aneuploidy, such as trisomy 18 or trisomy 21, in a pregnant woman. This method comprises multiple steps: the first step is to quantitatively determine the amount of one or more particular species of mRNA present in the pregnant woman's blood. The mRNA may encode hCG-β, hCRH, hPL, KISS1, TPFI2, PLAC1, or GAPDH. The second step is to compare the amount of mRNA obtained from the first step to a standard control representing the amount of mRNA encoding the same protein(s) in the blood of an average pregnant woman carrying a chromosomally normal fetus. An increase or a decrease in the mRNA level indicates an increased risk of having an aneuploid fetus.

In some embodiments, the mRNA used as a marker in the method encodes hCG-β. In some embodiments, the first step of the method is performed by RT-PCR, whereas in others this first step is carried out using a polynucleotide hybridization method or mass spectrometry. In some embodiments, the pregnant woman is during the first trimester of gestation, whereas in others the woman is during the second or third trimester of gestation. In some embodiments, the pregnant woman's blood is rendered acellular before it is used in the first step of the method. In some embodiments, plasma or serum is used in the first step of the method. In some embodiments, the increase is at least 2-fold. In other embodiments, the decrease is at lease 50%.

The invention also relates to a kit for detecting the presence of a fetus with a chromosomal aneuploidy (such as trisomy 18 or trisomy 21) in a pregnant woman. The kit comprises PCR primers for quantitatively determining the amount of one or more particular species of mRNA in the pregnant woman's blood. The mRNA may encode hCG-β, hCRH, hPL, KISS1, TPFI2, PLAC1, or GAPDH. The kit further comprises a standard control that represents the amount of mRNA encoding the same protein(s) in an average pregnant woman carrying a chromosomally normal fetus. A kit of the present invention may, in addition to or in place of the PCR primes, comprise one or more probes that can be used to quantitatively determine the amount of mRNA encoding hCG-β, hCRH, hPL, KISS1, TPFI2, PLAC1, or GAPDH.

A further aspect of the present invention relates to a method for diagnosing, monitoring, or predicting pre-term labor in a pregnant woman. This method comprises multiple steps: the first step is to quantitatively determine the amount of one or more particular species of mRNA present in the pregnant woman's blood. The mRNA may encode hCG-β, hCRH, hPL, KISS1, TPFI2, PLAC1, or GAPDH. The second step is to compare the amount of mRNA obtained from the first step to a standard control representing the amount of mRNA encoding the same protein(s) in the blood of an average woman who delivers or will deliver at term. An increase or a decrease in the mRNA level indicates pre-term labor or an increased risk of developing the condition.

In some embodiments, the first step of the method is performed by RT-PCR, whereas in others this first step is carried out using a polynucleotide hybridization method or mass spectrometry. In some embodiments, the pregnant woman is during the first trimester of gestation, whereas in others the woman is during the second or third trimester of gestation. In some embodiments, the pregnant woman's blood is rendered acellular before it is used in the first step of the method. In some embodiments, plasma or serum is used in the first step of the method. In some embodiments, the increase in the amount of mRNA from the standard control is more than 2-fold. In other embodiments, the decrease is at least 50%.

The invention also relates to a kit for diagnosing, monitoring, or predicting pre-term labor in a pregnant woman. The kit comprises PCR primers for quantitatively determining the amount of one or more particular species of mRNA in the pregnant woman's blood. The mRNA may encode hCG-β, hCRH, hPL, KISS1, TPFI2, PLAC1, or GAPDH. The kit further comprises a standard control that represents the amount of mRNA encoding the same protein(s) in an average pregnant woman who delivers or will deliver at term. A kit of the present invention may, in addition to or in place of the PCR primes, comprise one or more probes that can be used to quantitatively determine the amount of mRNA encoding hCG-β, hCRH, hPL, KISS1, TPFI2, PLAC1, or GAPDH.

An additional aspect of the invention relates to a method for detecting pregnancy in a woman. This method comprises multiple steps: the first step is to quantitatively determine the amount of one or more particular species of mRNA present in the woman's blood. The mRNA may encode hCG-β, hCRH, hPL, KISS1, TPFI2, or PLAC1. The second step is to compare the amount of mRNA obtained from the first step to a standard control representing the amount of mRNA encoding the same protein(s) in the blood of an average woman who is healthy and not pregnant. An increase in the mRNA level indicates pregnancy.

In some embodiments, the first step of the method is performed by RT-PCR, whereas in others this first step is carried out using a polynucleotide hybridization method or mass spectrometry. In some embodiments, the woman's blood is rendered acellular before it is used in the first step of the method. In some embodiments, plasma or serum is used in the first step of the method. In some embodiments, the increase in the amount of mRNA from the standard control is more than 2-fold. In other embodiments, the decrease is at least 50%.

The invention also relates to a kit for detecting pregnancy in a woman. The kit comprises PCR primers for quantitatively determining the amount of one or more particular species of mRNA in the pregnant woman's blood. The mRNA may encode hCG-β, hCRH, hPL, KISS1, TPFI2, or PLAC1. The kit further comprises a standard control that represents the amount of mRNA encoding the same protein(s) in an average woman who is healthy and not pregnant. A kit of the present invention may, in addition to or in place of the PCR primes, comprise one or more probes that can be used to quantitatively determine the amount of mRNA encoding hCG-β, hCRH, hPL, KISS1, TPFI2, or PLAC1.

DEFINITIONS

Figure 1:
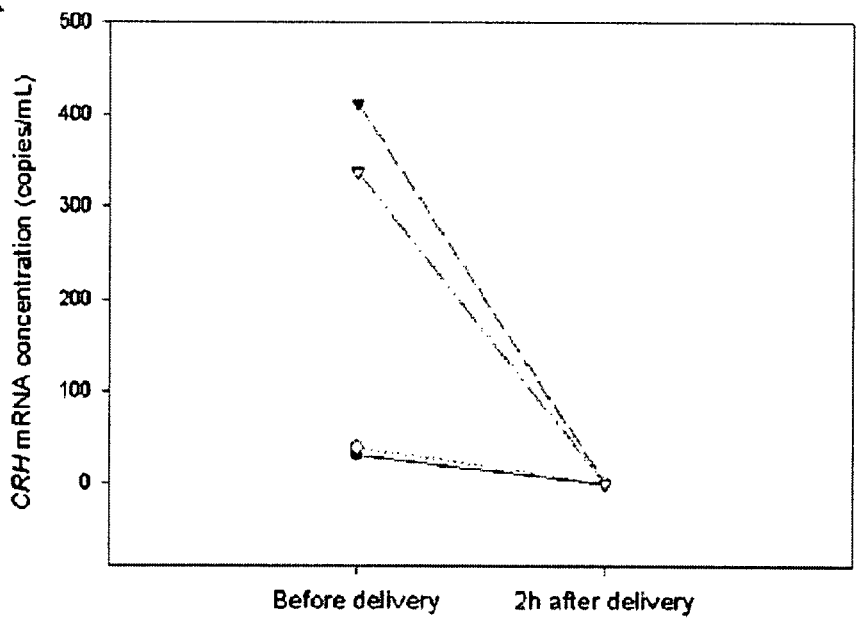
FIG. 1 demonstrates clearance of CRH mRNA from maternal plasma after delivery: A, CRH mRNA and B, GAPDH mRNA concentrations from maternal plasma before delivery and at 2 hours after delivery. Each line represents one plasma sample obtained from one subject.
Figure 1:
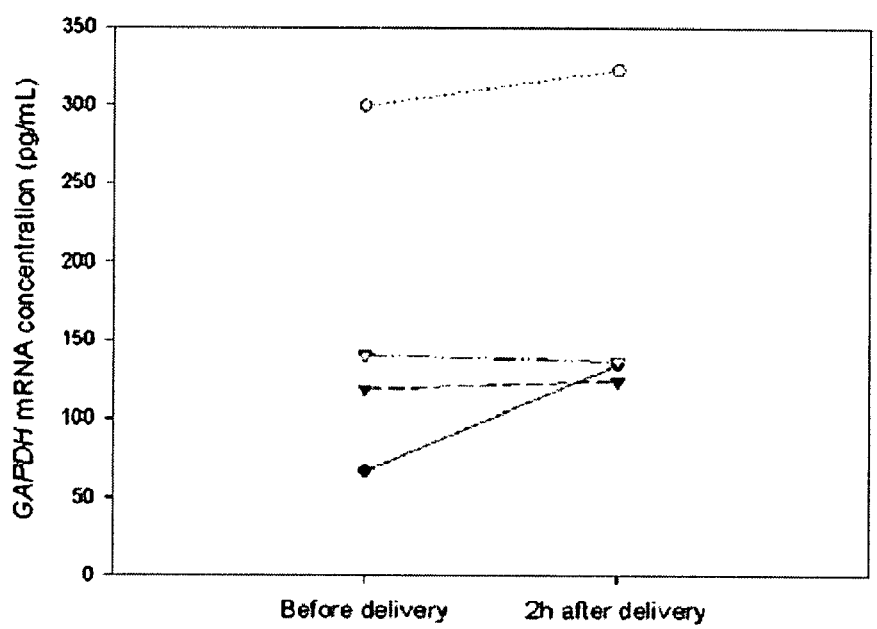

The term "preeclampsia" as used herein refers to a condition that occurs during pregnancy, the main symptom of which is various forms of high blood pressure often accompanied by the presence of proteins in the urine and edema (swelling). Preeclampsia, sometimes called toxemia of pregnancy, is related to a more serious disorder called "eclampsia," which is preeclampsia together with seizure. These conditions usually develop during the second half of pregnancy (after 20 weeks), though they may develop shortly after birth or before 20 weeks of pregnancy.

The term "chromosomal aneuploidy" as used herein refers to a state of chromosomal abnormality where the number of chromosomes is not an exact multiple of the usual haploid number: frequently, there is either an additional chromosome or one missing. The most common case of a chromosomal aneuploidy is a trisomy, where a single additional chromosome is present. For example, trisomy 18 is a chromosomal abnormality where a third chromosome 18 is found in a cell, whereas a third chromosome 21 is present in the cells of a patient suffering from trisomy 21.

In contrast to aneuploidy, "chromosomally normal" describes the state where the number of chromosomes is an exact multiple of the haploid number, such as twice the number of chromosomes found in a haploid, and each chromosome is present in the same number (except the sex chromosomes in the case of, e.g., male humans, where two different sex chromosomes, X and Y, are present at one copy each).

The term "pre-term labor" or "premature labor" as used herein refers to the condition where labor that begins more than three weeks before the full gestation period of about 40 weeks, which often leads to premature birth if not treated. In contrast, a pregnant woman who "delivers or will deliver at term" as used in this application refers to one that carries the fetus to its full term without ever developing pre-term labor.

The term "blood" as used herein refers to a blood sample or preparation from a pregnant woman or a woman being tested for possible pregnancy. The term encompasses whole blood or any fractions of blood that essentially contain no hematopoietic or any other types of cells of maternal or fetal origin, including platelets. "Blood" generally does not contain particular matters that may contain RNA of maternal or fetal origin. Examples of "blood" include plasma and serum. A blood sample that is essentially free of cells is also referred to as "acellular," where generally no platelets are present.

The term "average," as used in the context of describing a pregnant woman who is non-preeclamptic, carries a chromosomally normal fetus, or does not and will not develop pre-term labor, refers to certain characteristics, such as the level of mRNA encoding one or more particular fetal proteins found in maternal blood, that is representative of a randomly selected group of women who are non-preeclamptic, carry chromosomally normal fetuses, or do not and will not develop pre-term labor. This selected group should comprise a sufficient number of women such that the average level of mRNA encoding a particular fetal protein among these women reflects, with reasonable accuracy, the level of mRNA in the general population of healthy pregnant women with healthy fetuses. In addition, the selected group of women should have a similar gestational age to that of a woman whose blood is tested for indication of preeclampsia, fetal chromosomal aneuploidy, or pre-term labor. The preferred gestational age for practicing the present invention may vary depends on the disorder that is being screened for. For example, a pregnant woman is screened for the risk of preeclampsia preferably during the second trimester of the pregnancy, whereas fetal chromosomal aneuploidy is preferably screened for and diagnosed as early as possible. Moreover, the preferred gestational age for testing may also depend on the mRNA marker used in testing. For example, hPL mRNA is detectable throughout all three trimesters of pregnancy, whereas hCRH mRNA becomes increasingly detectable as gestation progresses.

The term "average" may be used similarly to refer to the amount of specified mRNA species that is representative of the amount found in the blood of a randomly selected group of healthy non-pregnant women.

Human chorionic gonadotropin β subunit (hCG-β), human placental lactogen (hPL), human corticotropin releasing hormone (hCRH), KiSS-1 metastasis-suppressor (KISS1), tissue factor pathway inhibitor 2 (TPFI2), placenta-specific 1 (PLAC1), and glyceraldehyde-3-phosphate dehydrogenase (GAPDH), as used herein, refer to the genes (including their variants and mutants) and their polynucleotide transcripts as exemplified by the sequences set forth in GenBank Accession Nos. NM_000737.2, NM_022640, NM_000756, U43527, NM_006528, BC022335, and BC014085, respectively. In some context, these terms may also refer to the proteins encoded by these genes.

"Standard control" as used herein refers to a sample suitable for the use of a method of the present invention, in order for quantitatively determining the amount of mRNA encoding a particular protein, e.g., hCG-β, hCRH, hPL, KISS1, TPFI2, PLAC1, or GAPDH. Such sample contains a known amount of the mRNA encoding a particular protein that closely reflects the average level of such mRNA in an average pregnant woman, who is non-preeclamptic, carries a chromosomally normal fetus, or does not and will not develop pre-term labor, as described above. Similarly, a "standard control" may be derived from an average healthy non-pregnant woman.

"An increase or a decrease in the amount of mRNA from the standard control" as used herein refers to a positive or negative change in amount from the standard control. An increase is preferably at least 2-fold, more preferably at least 5-fold, and most preferably at least 10-fold. Similarly, a decrease is preferably at least 50%, more preferably at least 80%, and most preferably at least 90%.

A "polynucleotide hybridization method" as used herein refers to a method for detecting the presence and/or quantity of a polynucleotide based on its ability to form Watson-Crick base-pairing, under appropriate hybridization conditions, with a polynucleotide probe of a known sequence. Examples of such hybridization methods include Southern blotting and Northern blotting.

"PCR primers" as used herein refer to oligonucleotides that can be used in a polymerase chain reaction (PCR) to amplify a nucleotide sequence originated from an mRNA encoding a protein of interest, such as hCG-β, hCRH, hPL, KISS1, TPFI2, PLAC1, or GAPDH. At least one of the PCR primers for amplification of a nucleotide sequence encoding an above-named protein should be sequence-specific for the protein.

DETAILED DESCRIPTION OF THE INVENTION

I. Introduction

The present invention provides, for the first time, methods and kits for diagnosing, monitoring, or predicting preeclampsia, fetal chromosomal aneuploidy (such as trisomy 18 and trisomy 21), and pre-term labor in pregnant women, as well as for detecting pregnancy in women, by analyzing the level of one or more of several mRNA species, i.e., those encoding, e.g., hCG-β, hCRH, hPL, KISS1, TPFI2, PLAC1, or GAPDH, present in the women's blood.

According to the invention, the amount of mRNA encoding hCG-β, hCRH, hPL, KISS1, TPFI2, PLAC1, or GAPDH in a maternal blood sample can be quantitatively determined, preferably following an amplification procedure, e.g., reverse transcriptase polymerase chain reaction (RT-PCR). The amount of one or more of the above-named mRNA species is then compared to a standard control having an mRNA level of the same species that is representative of an average pregnant woman without these pregnancy-related disorders at a similar gestational age. An increase or decrease in the mRNA level indicates the presence of or an increased risk of developing the disorders. The present invention thus provides a novel approach for diagnosis of preeclampsia, fetal chromosomal aneuploidy, and pre-term labor, which is non-invasive as well as gender- and polymorphism-independent.

Relying on the same methodology, by comparing the level of one or more of the mRNA species encoding hCG-β, hCRH, hPL, KISS1, TPFI2, or PLAC1 in a woman's blood to an established control value obtained from average non-pregnant woman, the present invention may be used to detect pregnancy.

II. Preparation of Blood Samples

A. Obtaining Blood Samples

The first step of practicing the present invention is to obtain a blood sample from a pregnant woman at a gestational age suitable for testing using a method of the present invention, or from a woman who is being tested for possible pregnancy. The suitable gestational age may vary depending on the disorder tested and sometimes the mRNA marker used, as discussed above. Collection of blood from a woman is performed in accordance with the standard protocol hospitals or clinics generally follow. An appropriate amount of peripheral blood, e.g., between 5-20 ml, is collected and maybe stored according to standard procedure prior to further preparation.

B. Preparing Acellular Blood Samples

The serum or plasma of a woman's blood is suitable for the present invention and can be obtained by well known methods. For example, a woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum is obtained through centrifugation following blood clotting. Centrifugation is typically conducted at an appropriate speed, e.g., 1,500-3,000×g, in a chilled environment, e.g., at a temperature of about 4-10° C. Plasma or serum may be subject to additional centrifugation steps before being transferred to a fresh tube for RNA extraction.

III. Quantitative Determination of the Amount of mRNA in a Woman's Blood

A. Extraction of mRNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a blood sample from a woman. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

B. PCR-Based Quantitative Determination of mRNA Level

Once mRNA is extracted from a woman's blood sample, the amount of mRNA encoding a protein of interest, e.g., hCG-β, hCRH, hPL, KISS1, TPFI2, PLAC1, or GAPDH, may be quantified. The preferred method for determining the mRNA level is an amplification-based method, e.g., by PCR.

Prior to the amplification step, a DNA copy (cDNA) of the mRNA of interest must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998.

C. Other Quantitative Methods

The mRNA of interest can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well known techniques (see, Sambrook and Russell, supra), the presence of a band of the same size as the standard control is an indication of the presence of a target mRNA, the amount of which may then be compared to the control based on the intensity of the band. Alternatively, oligonucleotide probes specific to mRNA encoding, e.g., hCG-β, hCRH, hPL, KISS1, TPFI2, PLAC1, or GAPDH, can be used to detect the presence of such mRNA species and indicate the amount of mRNA in comparison to the standard control, based on the intensity of signal imparted by the probe.

Sequence-specific probe hybridization is a well known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well known techniques and the detection is not a critical aspect of the present invention. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^{3}H$, $^{125}I$, $^{35}S$, $^{14}C$, or $^{32}P$, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255: 137-149, 1983.

IV. Establishing a Standard Control

In order to establish a standard control, a group of healthy pregnant women carrying healthy fetuses should first be selected. These women should be of similar gestational age, which is within the appropriate time period of pregnancy for screening of conditions such as preeclampsia, fetal chromosomal aneuploidy, and pre-term labor using the methods of the present invention. Similarly, a standard control is established using samples from a group of healthy non-pregnant women.

The healthy status of the selected pregnant women and the fetuses they are carrying should be confirmed by well established, routinely employed methods including but not limited to monitoring blood pressure of the women, recording the onset of labor, and conducting fetal genetic analysis using CVS and amniocentesis.

Furthermore, the selected group of healthy pregnant women carrying healthy fetuses or healthy non-pregnant women must be of a reasonable size, such that the average amount of mRNA encoding hCG-β, hCRH, hPL, KISS1, TPFI2, PLAC1, or GAPDH calculated from the group can be reasonably regarded as representative of the normal or average amount among the general population of healthy women carrying healthy fetuses or healthy non-pregnant women. Preferably, the selected group comprises at least 10 women.

Once an average value is established for the amount of mRNA encoding any one protein based on the individual values found in each women of the selected group, this values is considered a standard for the mRNA species. Any blood sample that contains a similar amount of mRNA of the same species can thus be used as a standard control. A solution containing mRNA encoding hCG-β, hCRH, hPL, KISS1, TPFI2, PLAC1, or GAPDH with a concentration of the established average of the same species can also be artificially assembled and serve as a standard control.

The following examples are provided by way of illustration only and not by way of limitation. Those of skill in the art will readily recognize a variety of non-critical parameters that could be changed or modified to yield essentially similar results.

EXAMPLES

Example 1

Elevated hCRH mRNA Level in Preeclamptic Women

A. Methods

Subjects

Peripheral blood samples were collected with informed consent and Research Ethics Committee approval from pregnant women, who attended the Department of Obstetrics and Gynecology at the Prince of Wales Hospital, Hong Kong.

In the first part of this study, blood samples were obtained from 10 healthy pregnant women during the third trimester of gestation. In the second part of the project, 4 pregnant women with uncomplicated pregnancy were recruited just prior to elective cesarean section. Peripheral blood samples were taken from these subjects just prior to delivery and at 2 hours post-delivery. In the third part of the study, two patient groups were studied: (a) 12 preeclamptic women and (b) 10 control pregnancies. The median gestational ages of the preeclamptic and control groups were 37 weeks and 38 weeks, respectively. Preeclampsia was defined on the basis of a sustained increase in diastolic blood pressure >110 mm Hg on one occasion or >90 mm Hg on two or more occasions at least 4 hours apart, with the presence of significant proteinuria in women with no history of hypertension. Significant proteinuria was defined as proteinuria >0.3 g/day or ≧2+ on dipstick testing in two clean-catch midstream urine specimens collected at least 4 hours apart. The control group included pregnant women with no preexisting medical diseases or antenatal complications.

Processing of Blood Samples

Blood samples were processed based on a previously reported protocol (Ng et al., *Clin. Chem.* 48:1212-1217, 2002). In brief, 10-mL blood samples were collected in EDTA-containing tubes, and centrifuged at 1600×g for 10 min at 4° C. Plasma was then carefully transferred into plain polypropylene tubes. The plasma samples were re-centrifuged at 16000×g for 10 min at 4° C., and the supernatants were collected into fresh polypropylene tubes.

RNA Extraction 1.6 mL of plasma was mixed with 2 mL of Trizol LS reagent (Invitrogen, Carlsbad, Calif.) and 0.4 mL of chloroform, as describe by Ng et al., supra. The mixture was centrifuged at 11,900×g for 15 min at 4° C. and the aqueous layer was transferred into new tubes. One volume of 70% ethanol was added to one volume of the aqueous layer. The mixture was then applied to an RNeasy mini column (Qiagen, Hilden, Germany) and was processed according to the manufacturer's recommendations. Total RNA was eluted with 30 μL of RNase-free water and stored at −80° C. DNase treatment (RNase-Free DNase Set, Qiagen, Hilden, Germany) was carried out to remove any contaminating DNA.

Real-Time Quantitative RT-PCR

One-step real-time quantitative RT-PCR was used for all mRNA quantitation according to the protocol provided by Ng et al., supra. The CRH primer sequences were 5'-GCCTC-CCATCTCCCTGGAT-3' (forward; SEQ ID NO:1) and 5'-TGTGAGCTTGCTGTGCTAACTG-3' (reverse; SEQ ID NO:2), and the dual-labelled fluorescent probe was 5'-(FAM) TCCTCCGGGAAGTCTTGGAAATGGC(TAMRA)-3' (SEQ ID NO:3). Calibration curves for CRH mRNA quantifications were prepared by serial dilutions of high performance liquid chromatography-purified single stranded synthetic DNA oligonucleotides (Genset Oligos, Singapore) specifying a 89 by CRH amplicon (Genbank Accession No. NM_000756), with concentrations ranging from $1\times10^7$ copies to $1\times10^1$ copies. Absolute concentrations of CRH mRNA were expressed as copies/mL of plasma. The sequences of the synthetic DNA oligonucleotides for CRH calibrations were 5'-GGAGCCTCCCATCTCCCTGGATCTCAC-CTTCCACCTCCTCCGGGAAGTCTTGGAAAT GGC-CAGGGCCGAGCAGTTAGCACAGCAAGCT-CACAGCA-3' (SEQ ID NO:4). A calibration curve for GAPDH quantification was prepared as previously described, with results expressed in pg/mL plasma (Ng et al., supra).

The RT-PCR reactions were set up according to the manufacturer's instructions (EZ rTth RNA PCR reagent set, Applied Biosystems, Foster City, Calif.) in a reaction volume of 25 μL. The fluorescent probes (Genset Oligos) were used at concentrations of 100 nM. The PCR primers (Genset Oligos) were used at a concentration of 200 nM for both the CRH and GAPDH systems. 5 μL of extracted plasma RNA was used for amplification. Each sample was analyzed in duplicate, and the corresponding calibration curve was run in parallel with each analysis. Samples were also tested to ensure they were negative for DNA by substituting the rTth polymerase with the AmpliTaq Gold enzyme (Applied Biosystems, Foster City, Calif.). No amplification was observed for this control analysis, indicating the specificity of the assays for the respective mRNA. Multiple negative water blanks were also included in every analysis.

The thermal profile used for the CRH and GAPDH analysis was as follows: the reaction was initiated at 50° C. for 2 min for the included uracil N-glycosylase to act, followed by reverse transcription at 60° C. for 30 min. After a 5-min denaturation at 95° C., 40 cycles of PCR was carried out using denaturation at 94° C. for 20 s and 1 min annealing/extension at 58° C. and 62° C. for the CRH and GAPDH systems, respectively.

Statistical Analysis

Statistical analysis was performed using the Sigma Stat 2.03 software (SPSS).

B. Results

Establishment of Real-Time Quantitative RT-PCR

To determine the quantitative performance of the CRH RT-PCR assay, we used this system to amplify serially diluted calibrators which were synthetic DNA oligonucleotides based on the CRH sequence. Previous data have shown that such single stranded oligonucleotides reliably mimic the products of the reverse transcription step and produce calibration curves that are identical to those obtained using T7-transcribed RNA (Bustin, *J. Mol. Endocrinol.* 25:169-193, 2000). The calibration curve for the CRH amplification systems demonstrated a dynamic range from $2.5 \times 10^1$ to $1 \times 10^6$ copies and had a correlation coefficient of 0.983. The sensitivities of the amplification steps of these assays were sufficient to detect 25 copies of the CRH target. To determine the precision of the whole analytical procedure involving RNA extraction, reverse transcription and amplification steps, we performed 10 replicate RNA extractions from a plasma sample obtained from a healthy pregnant woman (gestational age: 38 weeks) and subjected these extracted RNA samples to RT-PCR analysis. The coefficient of variation of the Ct values of these replicate analyses for CRH mRNA was 2.8%. The development and performance of the real-time quantitative GAPDH RT-PCR assay was previously described by Ng et al., supra.

Detectability of CRH mRNA in Maternal Plasma

To test whether CRH mRNA transcripts were detectable in maternal plasma, plasma samples from 10 pregnant women at the third trimester of pregnancy (gestational age 37 to 41 weeks) were analyzed by the CRH RT-PCR assay. CRH mRNA was detected in all tested samples. The median concentration of plasma CRH mRNA was 73 copies/mL (interquartile range: 51 to 177). As a positive control, GAPDH mRNA was detectable in all of these plasma samples.

Clearance of CRH mRNA from Maternal Plasma Following Delivery

To demonstrate that the maternal plasma CRH mRNA was derived from the feto-placental unit, we analyzed plasma from 4 women for CRH mRNA both before and at 2 hours post-delivery. Thus, CRH mRNA was detected in all 4 pre-delivery maternal plasma samples. In contrast, CRH mRNA was not detected in any of the post-delivery samples. GAPDH mRNA was detectable in all plasma samples, thus demonstrating the quality of the samples. The data are shown in FIGS. 1A and B.

Quantitative Analysis of CRH mRNA in the Plasma of Preeclamptic Pregnant Women

Figure 2:
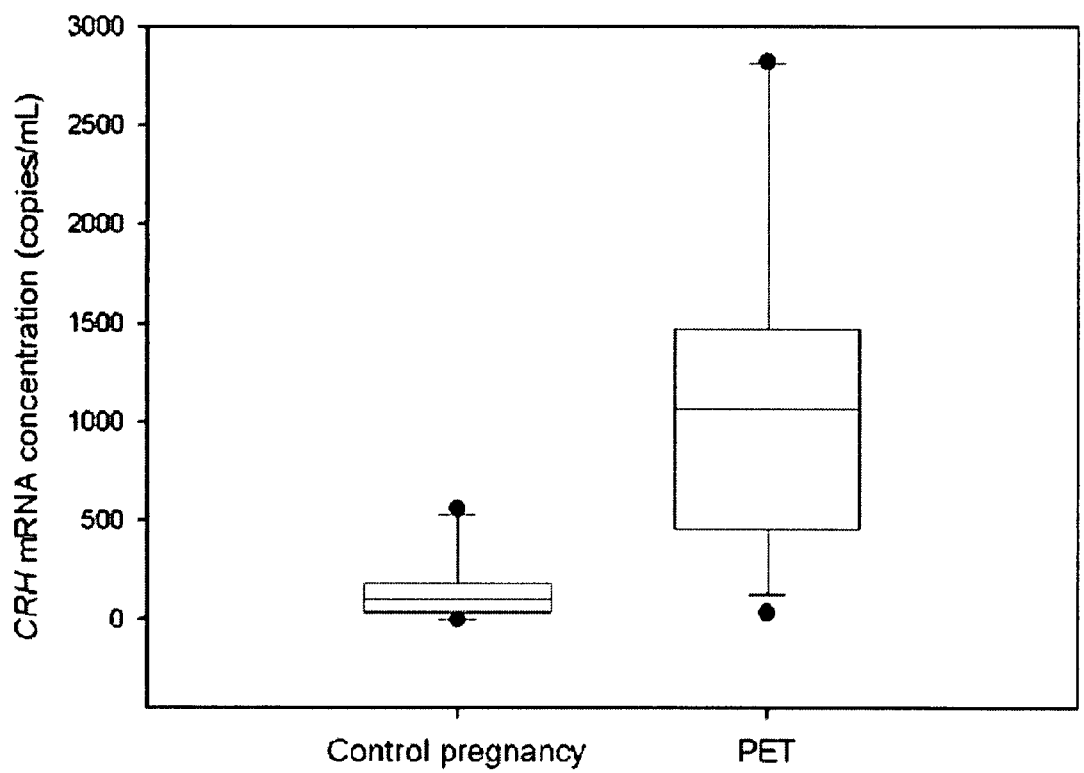
FIG. 2 is a box plot of CRH mRNA concentration in maternal plasma of preeclamptic and control groups. CRH mRNA concentrations are expressed in copies/mL. The lines inside the boxes denote the medians. The boxes mark the interval between the $25^{th}$ and $75^{th}$ percentiles. The whiskers denote the interval between the $10^{th}$ and $90^{th}$ percentiles. The filled circles mark the data points outside the $10^{th}$ and $90^{th}$ percentiles.

To compare the concentration of CRH mRNA in maternal plasma of preeclamptic and control pregnant women, plasma samples from 12 preeclamptic women and 10 control pregnant women with matched gestational age were obtained. FIG. 2 shows that the median CRH mRNA concentration in the plasma of preeclamptic women and control pregnancies were 1070 copies/mL (interquartile range, 535 to 1468) and 102 copies/mL (interquartile range, 51 to 158), respectively. The median plasma CRH mRNA concentrations were 10.5 times higher in preeclamptic than control pregnancies (Mann-Whitney test, P<0.001).

C. Conclusion

Plasma CRH mRNA represents a new molecular marker for preeclampsia. Compared with maternal plasma fetal DNA analysis, plasma RNA analysis has the advantage that it is gender- and polymorphism-independent. It is envisioned that plasma RNA analysis may ultimately allow non-invasive gene expression profiling of an unborn fetus.

Example 2

Detection of hPL and hCG-β mRNA in the Plasma of Pregnant Women

A. Methods

Subjects 15-ml blood samples were collected with informed consent and Research Ethics Committee approval from healthy women with singleton uncomplicated pregnancies, who attended the Department of Obstetrics and Gynecology at the Prince of Wales Hospital, Hong Kong.

Processing of Blood Samples

The blood samples were collected in EDTA-containing and plain tubes, and centrifuged at 1600×g for 10 min at 4° C. Plasma and serum were then carefully transferred into plain polypropylene tubes. The serum samples were stored at −20° C. for immunoassays for the hPL and hCG-β proteins. The plasma samples were re-centrifuged at 16000×g for 10 min at 4° C., and the supernatants were collected into fresh polypropylene tubes. All placental tissue samples were immediately stored in an RNA Later stabilizing solution (Ambion, Austin, Tex.) and kept at −80° C. until RNA extraction. For the filtration study, plasma samples were divided into three portions: two were individually passed through filters (Millex-GV; Millipore China Limited, Hong Kong) with pore sizes of either 0.45 μm or 5 μm. The third portion was not subjected to filtration.

RNA Extraction

For plasma samples, 1.6 ml of plasma was mixed with 2 ml of Trizol LS reagent (Invitrogen, Carlsbad, Calif.) and 0.4 ml of chloroform according to the protocol of Ng et al., supra. For placental tissues, samples were homogenized in Trizol reagent (Invitrogen) and chloroform was then added according to the manufacturer's recommendations. The mixture was centrifuged at 11,900×g for 15 min at 4° C. and the aqueous layer was transferred into new tubes. One volume of 70% ethanol was added to one volume of the aqueous layer. The mixture was then applied to an RNeasy mini column (RNeasy Mini Kit, Qiagen, Hilden, Germany) and was processed according to the manufacturer's recommendations. Total RNA was eluted with 30 μl of RNase-free water and stored at −80° C. DNase treatment was carried out to remove any contaminating DNA (RNase-Free DNase Set, Qiagen, Hilden, Germany).

Real-Time Quantitative RT-PCR

One-step real-time quantitative RT-PCR was used for all mRNA quantitation as described by Ng et al., supra. The primers for all of the hPL, hCG-β and GAPDH RT-PCR assays were intron-spanning. The hPL primer sequences were 5'-CATGACTCCCAGACCTCCTTC-3' (sense; SEQ ID NO:5) and 5'-TGCGGAGCAGCTCTAGATTG-3' (antisense; SEQ ID NO:6), and the dual-labeled fluorescent probe was 5'-(FAM)TTCTGTTGCGTTTCCTCCATGTTGG (TAMRA)-3' (SEQ ID NO:7). The hCG-β primer sequences were 5'-CTACTGCCCCACCATGACCC-3' (sense; SEQ ID NO:8) and 5'-TGGACTCGAAGCGCACATC-3' (antisense; SEQ ID NO:9), and the dual-labeled fluorescent probe was 5'-(FAM)CCTGCCTCAGGTGGTGTGCAACTAC (TAMRA)-3' (SEQ ID NO:10). Calibration curves for hPL and hCG-β quantifications were prepared by serial dilutions of high performance liquid chromatography-purified single stranded synthetic DNA oligonucleotides (Genset Oligos, Singapore) specifying the hPL and hCG-β amplicons, respectively, with concentrations ranging from $1 \times 10^7$ copies to $1 \times 10^1$ copies. These assays were able to detect 100 copies of the respective calibrator targets. Absolute concentrations of hPL and hCG-β mRNA were expressed as copies/ml of plasma. Previous data have shown that such single stranded oligonucleotides reliably mimic the products of the reverse transcription step and produce calibration curves that are identical to those obtained using T7-transcribed RNA (Bustin, supra). The sequences of the synthetic DNA oligonucleotides for hPL and hCG-β calibrations were 5'-TGCGGAG-CAGCTCTAGATTGGATTTCTGTTGCGTTTCCTCCAT-GTTGGAGGGTGTCG GAATAGAGTCTGAGAAGCA-GAAGGAGGTCTGGGAGTCATGC-3' (SEQ ID NO:11) and 5'-GATGGACTCGAAGCGCACATCGCGG-TAGTTGCACACCACCTGAGGCAGGGCCGGCA GGACCCCCTGCAGCACGCGGGTCATG-GTGGGGCAGTAGCC-3' (SEQ ID NO:12), respectively. A calibration curve for GAPDH quantification was prepared as previously described by Ng et al, supra, with results expressed in pg/ml plasma.

The RT-PCR reactions were set up according to the manufacturer's instructions (EZ rTth RNA PCR reagent set, Applied Biosystems, Foster City, Calif.) in a reaction volume of 50 μl. The fluorescent probes (Genset Oligos) were used at concentrations of 100 nM. The PCR primers (Genset Oligos) were used at a concentration of 300 nM for hPL and 200 nM for both hCG-β and GAPDH. 5 μl of extracted plasma RNA and 0.1 ng of extracted total placental RNA were used for amplification. Each sample was analyzed in duplicate, and the corresponding calibration curve was run in parallel for each analysis. Samples were also tested to ensure they were negative for DNA by substituting the rTth polymerase with the AmpliTaq Gold enzyme (Applied Biosystems, Foster City, Calif.). No amplification was observed for this control analysis, indicating the specificity of the assays for the respective mRNA. Multiple negative water blanks were also included in every analysis.

The thermal profile used for the hPL, hCG-β, and GAPDH analysis was as follows: the reaction was initiated at 50° C. for 2 min for the included uracil N-glycosylase to act, followed by reverse transcription at 60° C. for 30 min. After a 5-min denaturation at 95° C., 40 cycles of PCR was carried out using denaturation at 94° C. for 20 s and 1 min annealing/extension at 56° C., 58° C. and 60° C. for hPL, hCG-β, and GAPDH, respectively.

Replicate RNA extraction and RT-PCR analysis indicated that the coefficients of variation of Ct values of the analytical system for hPL and hCG-β mRNA were 2.3% and 3.2%, respectively.

Protein Assays

The hPL and hCG protein concentrations were determined in maternal serum by a radioimmunoassay (Diagnostic Products Corp., Los Angeles, Calif.) and an electrochemiluminescence immunoassay (Roche modular E170), respectively.

B. Results

Detectability and Stability of Placental mRNA in Maternal Blood

We obtained peripheral blood samples from 10 pregnant women (gestational age 7 to 14 weeks). In half of the blood sample from each subject, plasma harvesting and RNA extraction were performed immediately upon arrival at the laboratory (within 1 hour of venesection). To test if hPL and hCG-β mRNA transcripts were detectable in maternal plasma, we analyzed the extracted RNA using the respective real-time RT-PCR assays. We observed hPL and hCG-β mRNA signals in all 10 plasma samples. These results demonstrated that placental mRNA was indeed detectable in the plasma of pregnant women. As a positive control, GAPDH mRNA was also detectable in all of these plasma samples.

To investigate the stability of placental mRNA in maternal blood, we left the remaining aliquot from each of these maternal blood samples for 24 hours at room temperature. We then extracted RNA from these samples and measured the levels of hPL, hCG-β, and GAPDH transcripts. No significant difference was observed in the levels of hPL and hCG-β mRNA transcripts, while the GAPDH mRNA was significantly higher in samples that had been left at room temperature for 24 hours than those that had been processed immediately (Wilcoxon test, P=0.770 for the hPL study; P=0.275 for the hCG-β study; P<0.05 for the GAPDH study). These results indicate that hPL and hCG-β mRNA in plasma was stable for up to 24 hours at room temperature.

Variation of Circulating Placental mRNA with Gestational Age

Figure 3:
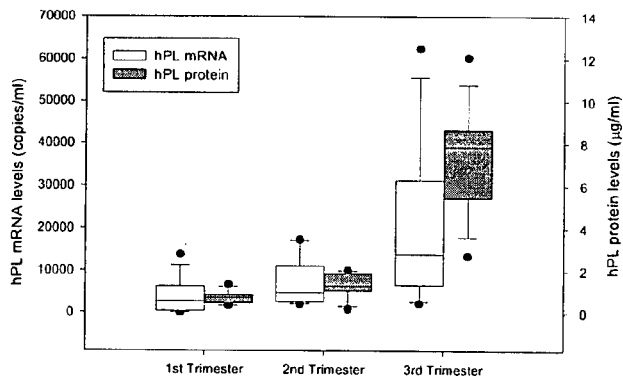
FIG. 3 shows the levels of placenta-derived mRNA in maternal plasma in normal pregnancy. (A) Box plot of hPL mRNA in maternal plasma and protein levels in maternal serum at different stages of gestation. (B) Box plot of βhCG mRNA in maternal plasma and hCG protein levels in maternal serum at different stages of gestation. The lines inside the boxes denote the medians. The boxes mark the interval between the $25^{th}$ and $75^{th}$ percentiles. The whiskers denote the interval between the $10^{th}$ and $90^{th}$ percentiles. The filled circles mark the data points outside the $10^{th}$ and $90^{th}$ percentiles. (C) Correlation between hPL mRNA in maternal plasma and protein levels in maternal serum. (D) Correlation between βhCG mRNA in maternal plasma and protein levels in maternal serum.
Figure 3:
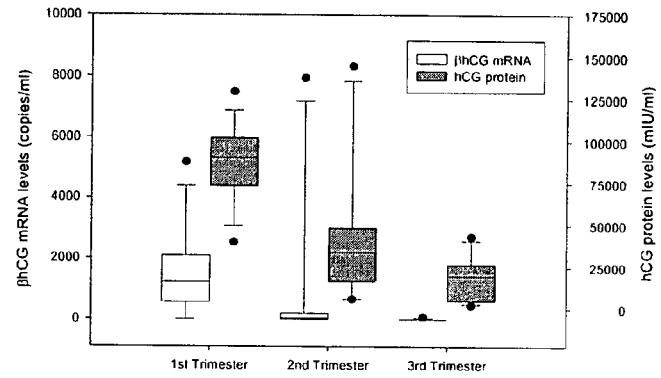
Figure 3:
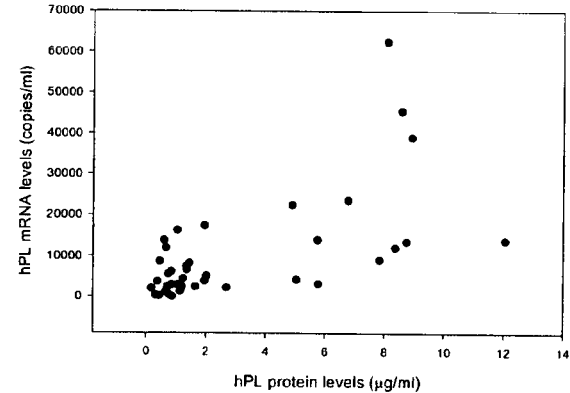
Figure 3:
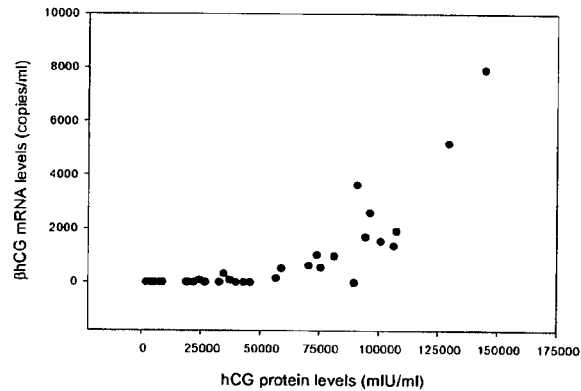

We obtained plasma samples from 39 pregnant women at different stages of gestation. We detected hPL mRNA in 100% (39 out of 39) of all plasma tested in all three trimesters of pregnancy. For hCG-β mRNA, the detection rates were 100% (14/14) for first trimester (gestational age: 7 to 14 weeks) samples, 42% (5/12) for second trimester (gestational age: 15 to 23 weeks) samples and 7.7% (1/13) for third trimester (gestational age: 35 to 41 weeks) samples. In the first-trimester plasma samples, the median levels of hPL and hCG-β mRNA were 2671 (interquartile range: 375 to 6217) and 1205 copies/ml (interquartile range: 566 to 1927), respectively (FIGS. 3A and B). The median levels of plasma hPL and hCG-β mRNA from second-trimester pregnancies were 4784 (interquartile range: 2679 to 10139) and 0 copies/ml (interquartile range: 0 to 125), respectively. In the third-trimester plasma samples, the median levels of plasma hPL and hCG-β mRNA were 13869 (interquartile range: 7829 to 27434) and 0 copies/ml (interquartile range: 0 to 0), respectively. Overall, circulating hPL and hCG-β mRNA levels show an increasing and a decreasing trend, respectively, with gestational age. The corresponding levels of hPL and hCG-β proteins were also determined (FIGS. 3A and B). The overall gestational variation of circulating hPL and hCG-β mRNA shows a resemblance to the trends exhibited by the corresponding proteins (Pearson correlation analysis, r=0.622; P<0.001 for hPL and r=0.784; P<0.001 for hCG-β, FIGS. 3C and D).

Rapid Clearance of Placental mRNA from Maternal Plasma Following Delivery

Figure 4:
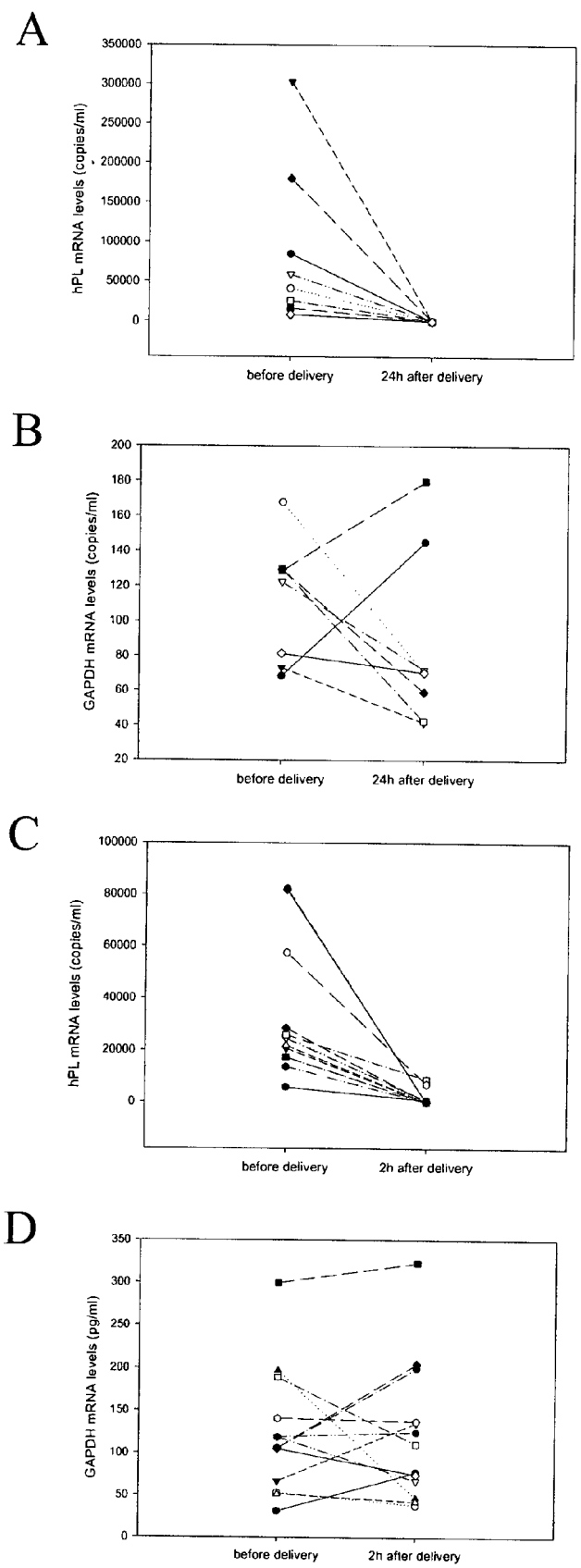
FIG. 4 shows the clearance of hPL mRNA from maternal plasma after delivery. (A) Maternal plasma hPL mRNA levels and (B) Maternal plasma GAPDH mRNA levels before delivery and at 24 hours after delivery. The results of 8 plasma samples are shown and each line represents one plasma sample obtained from one subject. (C) Maternal plasma hPL mRNA levels and (D) Maternal plasma GAPDH mRNA levels before delivery and at 2 hours after delivery. The results of 13 plasma samples are shown and each line represents one plasma sample obtained from one subject.

We next investigated if delivery would result in the clearance of placental mRNA from maternal plasma. We chose hPL mRNA as our target because of the relative abundance of hPL mRNA in maternal plasma during the last trimester of pregnancy (gestational age of studied subjects: 38 to 42 weeks). In 8 pre-delivery plasma samples, the median level of hPL mRNA transcripts was 50004 copies/ml. hPL mRNA was not detected in any of the postpartum samples at 24 hours after delivery (FIG. 4A). As a control, GAPDH mRNA was detected in all pre- and post-delivery plasma samples (FIG. 4B). No systematic alteration in maternal plasma GAPDH mRNA levels was observed (Wilcoxon test, P=0.313). We next investigated if clearance of circulating hPL mRNA might be observable if a shorter post-partum time-point (2 hours) was studied. In 13 subjects recruited for this second study, the median pre-delivery level of hPL mRNA was 24499 copies/ml (FIG. 4C). Nine of the thirteen women had no detectable plasma placental RNA by 2 hours postpartum. The remaining subjects had approximately 66-97% of maternal plasma fetal RNA cleared by 2 hours after delivery. We detected GAPDH mRNA in all plasma samples, thus demonstrating the quality of the samples (FIG. 4D). No systematic alteration in maternal plasma GAPDH mRNA levels was observed (Wilcoxon test, P=1.000).

Example 3

Elevation in Maternal Plasma GAPDH mRNA in Preeclamptic Women

Pregnant women attending the Department of Obstetrics and Gynecology at the Prince of Wales Hospital were recruited with informed consent. Preeclampsia was diagnosed using the criteria as indicated in Example 1.

A. Methods

Maternal blood samples were taken into heparinized tubes and processed as indicated in Example 1. Plasma RNA was extracted and GAPDH mRNA level was quantified as indicated in Example 1.

B. Results

Figure 5:
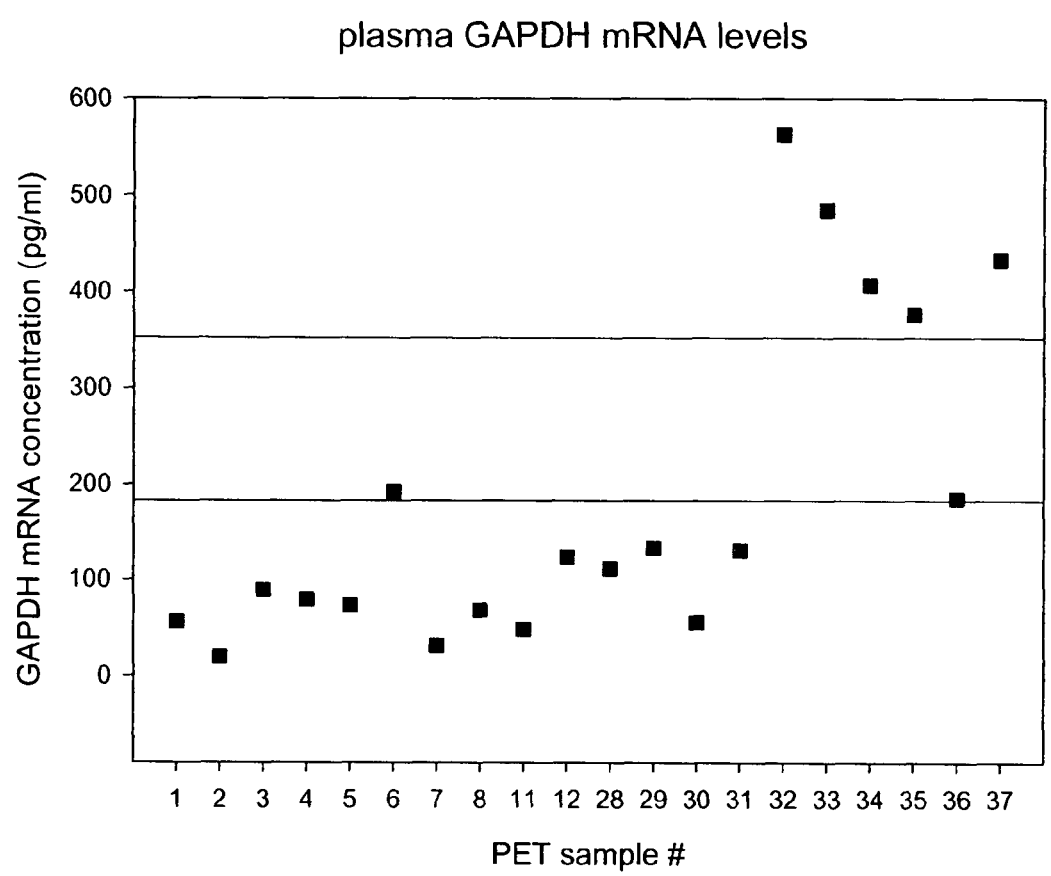
FIG. 5 illustrates the amount of GAPDH mRNA in maternal plasma. Samples 1-12 are from normal pregnant women and 28-37 are from preeclamptic women.

Elevation in maternal plasma GAPDH mRNA concentrations was observed in the preeclamptic group, when compared with the control group (FIG. 5). The median maternal plasma GAPDH mRNA concentrations in control and preeclamptic subjects were 70 pg/ml and 281 pg/ml, respectively. The difference is statistically significant (Mann-Whitney test, p<0.005).

C. Conclusion

Maternal plasma GAPDH mRNA is a new noninvasive marker for preeclampsia.

Example 4 hCGβ mRNA Concentrations in Maternal Serum in Aneuploid Pregnancies

A. Methods

The concentration of βhCG mRNA was measured by real-time quantitative RT-PCR in first-trimester serum samples collected from 141 pregnant women investigated between January and August 2003. In all studied subjects, chorionic villous sampling (CVS) for fetal karyotyping was carried out. All maternal blood samples were collected immediately before CVS. Blood samples were collected in plain tubes, and centrifuged at 1600×g for 10 min at 4° C. Serum was then transferred into plain polypropylene tubes. 3.2 mL serum was immediately stored in 4 mL Trizol and kept at −80° C. until RNA extraction. Serum RNA was extracted from 1.6 mL of serum by a modified RNeasy RNA Mini Kit (Qiagen, Hilden, Germany) as previously described (Ng et al., *Proc. Natl. Acad. Sci. USA*, 100:4748-4753, 2003). Total RNA was eluted with 30 μL of RNase-free water and stored at −80° C. DNase treatment was carried out to remove any contaminating DNA (RNase-Free DNase Set, Qiagen, Hilden, Germany).

One-step real-time quantitative RT-PCR was used for βhCG mRNA quantification, as described by Ng et al., *Proc. Natl. Acad. Sci. USA*, 100:4748-4753, 2003. The RT-PCR reactions were set up in a reaction volume of 25 μL. The primers and fluorescent probe were used at concentrations of 300 nM and 100 nM, respectively. 6 μL of extracted serum RNA was used for amplification. The thermal profile used for the analysis was as follows: the reaction was initiated at 50° C. for 2 min for the included uracil N-glycosylase to act, followed by reverse transcription at 60° C. for 30 min. After a 5-min denaturation at 95° C., 40 cycles of PCR was carried out using denaturation at 94° C. for 20 s and 1 min annealing/extension at 57° C. The sensitivity, linearity, and precision of the assay have been established by Ng et al., *Proc. Natl. Acad. Sci. USA*, 100:4748-4753, 2003. As little as 100 copies of the synthetic oligonucleotide were detectable in the reaction mixture. Concentrations of serum hCGβ mRNA were expressed as copies/mL of serum. As no recovery experiments had been done, the reported concentrations (copies/mL) were minimum estimates.

Among the 149 pregnant women recruited, 15 women carried fetuses with trisomy 21 and 11 carried fetuses with trisomy 18. The remaining of 123 cases had euploid fetuses and served as controls. The median gestational age of the controls was 12.5 weeks (range: 11.2 to 14.3 weeks). The median gestational ages of the trisomy 21 and trisomy 18 cases were 12.5 weeks (range: 12.1 to 14.2 weeks) and 12.3 weeks (range: 11.4 to 14.1 weeks), respectively. No significant difference of the gestational age was observed amongst the three cohorts (Kruskal-Wallis, P=0.706).

B. Results

Figure 6:
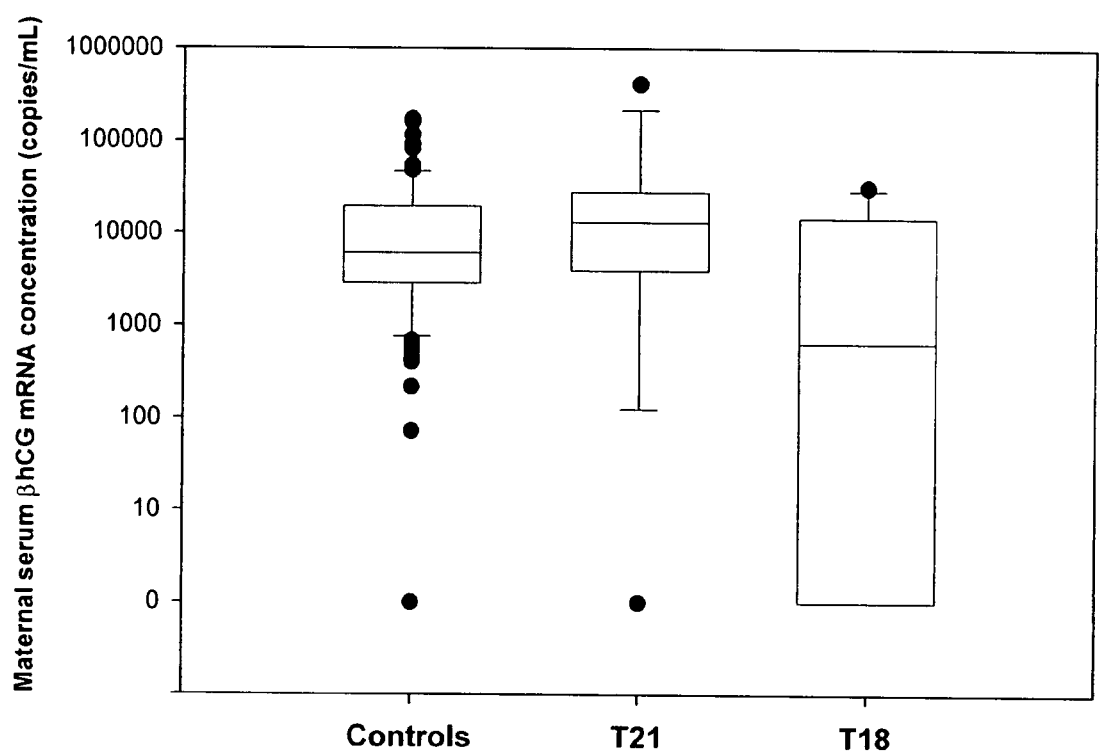
FIG. 6 depicts maternal serum hCGβ mRNA concentrations in first-trimester aneuploid and control pregnancies. Box plot of hCGβ mRNA concentrations (common logarithmic scale) in sera of control, trisomy 21 (T21) and trisomy 18 (T18) pregnancies. The lines inside the boxes denote the medians. The boxes mark the interval between the $25^{th}$ and $75^{th}$ percentiles. The whiskers denote the interval between the $10^{th}$ and $90^{th}$ percentiles. The filled circles mark the data points outside the $10^{th}$ and $90^{th}$ percentiles.

Maternal serum samples of the 149 studied cases were subjected to hCGβ mRNA quantification. hCGβ mRNA could be detected in the maternal serum of 140 out of 149 pregnancies (94%). In the control cohort, the detection rate of hCGβ mRNA was 96.7% (119 of 123). For the trisomy 21 and trisomy 18 cohorts, the detection rates were 93.3% (14 of 15) and 63.6% (7 of 11), respectively. The median serum hCGβ mRNA concentrations of the three cohorts were 6108 copies/mL (interquartile range: 2867 to 19249 copies/mL) for the control cohort, 13165 copies/mL (interquartile range: 4403 to 25265 copies/mL) for the trisomy 21 cohort, and 652 copies/mL (interquartile range: 0 to 11662 copies/mL) for the trisomy 18 cohort (FIG. 6). The difference in the median hCGβ mRNA concentrations among the three cohorts is statistically significant (Kruskal-Wallis, P=0.024). Pairwise multiple comparisons were performed and showed that significant differences were observed between the trisomy 18 and control cases (Dunn's test, P<0.05), and between the trisomy 18 and trisomy 21 cases (Dunn's test, P<0.05). No statistically significant difference was observed between the serum hCGβ mRNA concentrations in trisomy 21 and control cases (Dunn's test, P>0.05), due to a limited sample size. Given a larger sample size, however, a difference of statistically significance will be established.

C. Conclusion

This study has confirmed that circulating hCGβ mRNA is easily and robustly detectable in the serum of first-trimester pregnant women, with a detection rate of 94%. These data demonstrate that the median concentration of serum hCGβ mRNA in trisomy 18 pregnancies was about 10% of the median concentration in the control pregnancies and statistically significant difference was observed. On the other hand, although the median concentration of serum hCGβ mRNA in trisomy 21 pregnancies was 2.2-fold higher than the median concentration in the control pregnancies, no statistically significant difference was observed due to limited sample size. Such statistically significant difference is expected in a study of larger scale. These data offer the first demonstration that circulating hCGβ mRNA concentration in the first-trimester serum of trisomy 18 pregnancies is significantly reduced, whereas the circulating hCGβ mRNA concentration is elevated in trisomy 21 pregnancies.

These data indicate the diagnostic usefulness of circulating hCGβ mRNA as a marker for predicting aneuploid, e.g., trisomy 18 and trisomy 21, pregnancies. An overlap in the hCGβ mRNA concentrations between the trisomy 18 and control cases was observed in this study. This implies that a relatively low sensitivity and specificity might result if maternal serum hCGβ mRNA measurement is used as the sole predictor for pregnancies with trisomy 18. Additional markers, such as hPL, hCRH, KiSS-1, TPFI2, and PLAC1, can be used in combination with hCGβ to achieve enhanced sensitivity and specificity in diagnosis.

Example 5

Identification of Placental mRNA in Maternal Plasma

A. Methods

The study was performed in two stages. Initially, placental tissue gene expression profiles in both the first and third trimesters of pregnancy were systematically identified using oligonucleotide microarrays. This was followed by the development of a number of assays based on real-time quantitative reverse-transcriptase polymerase chain reaction (QRT-PCR) for the detection of six of the identified placental-expressed genes in maternal plasma. The RNA transcripts studied were assessed both for their detectability in maternal plasma, and the correlation of their levels between plasma and placental tissues. All placental and blood samples used in this study were collected with informed consent from healthy women with singleton uncomplicated pregnancies, who attended the Department of Obstetrics and Gynaecology at the Prince of Wales Hospital, Hong Kong.

Identification of Placental Gene Expression Profiles

Five each of first-trimester (gestational age range: 9 to 12 weeks) and third-trimester (gestational age range: 38 to 40 weeks) placental tissue samples were obtained from pregnant women by chorionic villus sampling (CVS) before abortions or immediately after elective caesarean delivery, respectively. The placental tissue samples were stored in RNAlater™ (Ambion®, Austin, Tex.) immediately upon collection and kept at −80° C. until RNA extraction. 6 mL of peripheral blood was collected concurrently at the time of tissue collection and stored in PAXgene™ Blood RNA Tubes (PreAnalytiX, Hombrechtikon, Switzerland).

Total RNA from placental tissues were extracted with the Trizol Reagent (Invitrogen, Carlsbad, Calif.) and purified with an RNeasy mini-kit (Qiagen, Hilden, Germany) following manufacturer's protocols. Total RNA from peripheral blood was extracted by the PAXgene™ Blood RNA Kit (PreAnalytiX, Hombrechtikon, Switzerland) according to manufacturer's instructions, with the inclusion of DNase treatment (RNase-Free DNase Set, Qiagen, Hilden, Germany).

For each sample, ten microgrammes of the extracted RNA were labeled and hybridized to the GeneChip® Human Genome U133A Arrays (Affymetrix, Santa Clara, Calif.) according to the manufacturer's instructions. After hybridization, each array was washed and stained in a GeneChip® Fluidics Station 400 (Affymetrix, Santa Clara, Calif.). The chips were scanned with the GeneArray Scanner (Affymetrix, Santa Clara, Calif.) and analyzed using the GeneChip® Microarray Suite 5.0 (Affymetrix).

Quantitative Assessment of Placental-Expressed RNA Transcripts in Maternal Plasma by Real-Time QRT-PCR Paired placentas and maternal whole blood samples from 10 first and 10 third trimester pregnancies were collected. Peripheral blood samples from 10 pregnant women before and after delivery were also recruited. The placental tissues were processed as described above. 12 mL of the blood samples was collected into EDTA tubes and was centrifuged at 1600×g for 10 min at 4° C. Plasma was then carefully transferred into plain polypropylene tubes. The plasma samples were re-centrifuged at 16000×g for 10 min at 4° C. Supernatants were collected into fresh polypropylene tubes. RNA extraction from maternal plasma was performed as previously described by Ng. et al., *Clin. Chem.*, 48:1212-1217, 2002. DNase treatment (RNase-Free DNase Set, Qiagen, Hilden, Germany) was carried out to remove any contaminating DNA.

The study focused on the assessment of six placental-expressed mRNA transcripts that were identified from the placental microarray gene expression profiles, including human placental lactogen (hPL), human chorionic gonadotropin beta subunit (βhCG), corticotropin releasing hormone (CRH), tissue factor pathway inhibitor 2 (TFPI2), KiSS-1 metastasis-suppressor (KISS1) and placenta-specific 1 (PLAC1). Quantitative analysis of two non-placental-specific transcripts, glyceraldehyde-3-phosphate dehydrogenase (GAPDH) and beta-haemoglobin (β-globin) mRNA was performed as controls.

QRT-PCR assays for the detection of GAPDH, hPL, hCGβ, and CRH mRNA were described previously (Ng. et al., *Clin. Chem.*, 48:1212-1217, 2002; Ng et al., *Proc. Natl. Acad. Sci. USA*, 100:4748-4753, 2003; and Ng et al., *Clin. Chem.*, 49:727-731, 2003). The primer sequences for the TFPI2 assay were 5'-ACAAATTTCTACACCTGGGAGGC-3' (sense; SEQ ID NO:13) and 5'-CGGCAAACTTTGG-GAACTTTT-3' (antisense; SEQ ID NO:14), and the dual-labeled fluorescent probe was 5'-(FAM) TGCGACGATGCTTGCTGGAGGA (TAMRA)-3' (SEQ ID NO:15). FAM and TAMRA represented 6-carboxyfluorescein and 6-carboxytetramethylrhodamine, respectively. The primer sequences for KISS1 quantification were 5'-GC-CCAGGCCAGGACTGA-3' (sense; SEQ ID NO:16) and 5'-GCCAAGAAACCAGTGAGTTCATC-3' (antisense; SEQ ID NO:17), and the dual-labelled fluorescent probe was 5'-(FAM) CCTCAAGGCACTTCTAGGACCTGGCTCTTC (TAMRA)-3' (SEQ ID NO:18). The PLAC1 assay primer sequences were 5'ATTATCCCCAGCTGCCAGAA-3' (sense; SEQ ID NO:19) and 5'-GCAGCCAATCAGATAAT-GAACCA-3' (antisense; SEQ ID NO:20), and the dual-labelled fluorescent probe was 5'-(FAM) AAGAAATCCT-CACTGGACGGCTTCCTG (TAMRA)-3' (SEQ ID NO:21). The primer sequences for the β-globin assay were 5'-GCTG-CACTGTGACAAGCTGC-3' (sense; SEQ ID NO:22) and 5' GCACACAGACCAGCACGTTG-3' (antisense; SEQ ID NO:23), and the fluorescent probe was 5'-(FAM) CGTG-GATCCTGAGAACTTCAGGCTC (TAMRA)-3' (SEQ ID NO:24).

Calibration curves for hPL, βhCG, CRH, TFPI2, KISS1, PLAC1, and β-globin mRNA quantification were prepared by serial dilutions of high performance liquid chromatography-purified single stranded synthetic DNA oligonucleotides as described by Bustin et al., *J. Mol. Endocrinol.*, 25:169-193, 2000 (Genset Oligos, Singapore) specific for the respective amplicons, with concentrations ranging from $1 \times 10^6$ copies to 10 copies. The sequences of the synthetic DNA oligonucleotides for hPL, βhCG and CRH calibration were described previously (see Ng et al., *Proc. Natl. Acad. Sci. USA*, 100:

4748-4753, 2003 and Ng et al., *Clin. Chem.*, 49:727-731, 2003). The sequences of the synthetic DNA oligonucleotides for TFPI2, KISS1, PLAC1, and β-globin calibrators were 5'-CGCCAACAATTTCTACACCTGGGAGGCT-TGCGACGATGCTTGCTGGAGGATAGAAA AAGTTC-CCAAAGTTTGCCGGCTG-3' (SEQ ID NO:25), 5'-CTGC-CCAGGCCAGGACTGAGGCAAGCCTCAAGGCACTT-CTAGGACCTGGCTCTTCTC ACCAAGATGAACT-CACTGGTTTCTTGGCAG-3' (SEQ ID NO:26), 5'-ACAAATTATCCCCAGCTGCCAGAAGAA-GAAATCCTCACTGGACGGCTTCCTGTTTCC TGTG-GTTCATTATCTGATTGGCTGCAGG-3' (SEQ ID NO:27) and 5-TGAGCTGCACTGTGACAAGCTGCACGTG-GATCCTGAGAACTTCAGGCTCCTGGGCAA CGT-GCTGGTCTGTGTGCTGG-3' (SEQ ID NO:28), respectively. Except for GAPDH mRNA, absolute concentrations of all transcripts were expressed as copies/ng of total placental RNA and copies/ml of plasma for placental tissues and maternal plasma, respectively. The calibration curve for GAPDH quantification was prepared by serial dilutions of human total RNA (Ng. et al., *Clin. Chem.*, 48:1212-1217, 2002).

The QRT-PCR reactions were set up according to the manufacturer's instructions (EZ rTth RNA PCR reagent set, Applied Biosystems, Foster City, Calif., USA) in a reaction volume of 50 µl. The QRT-PCR assays were carried out in a combined thermal cycler and fluorescent detector (ABI Prism 7700, Applied Biosystems, Foster City, Calif., USA). The reaction conditions for the GAPDH, hPL, βhCG and CRH QRT-PCR assays were described previously (Ng. et al., *Clin. Chem.*, 48:1212-1217, 2002; Ng et al., *Proc. Natl. Acad. Sci. USA*, 100:4748-4753, 2003; and Ng et al., *Clin. Chem.*, 49:727-731, 2003). For the other three transcripts, the PCR primers (Geneset Oligos, Singapore) were used at concentrations of 200 nM for TFPI2 and β-globin, 300 nM for KISS1 and 400 nM for PLAC1. The fluorescent probes (Applied Biosystems, Foster City, Calif., USA) were used at concentrations of 80 nM for TFPI2, 150 nM for KISS1, 200 nM for PLAC1 and 300 nM for β-globin. Before performing QRT-PCR, contaminating DNA in the extracted placental tissue RNA was removed by DNase I digestion (Invitrogen, Carlsbad, Calif.) according to manufacturer's recommendations. 0.4 ng of extracted placental RNA and 6 µl of extracted plasma RNA were used for amplification. Multiple negative water blanks were included in every analysis.

The thermal profiles used for TFPI2, KISS1, PLAC1, and β-globin mRNA analysis were as follows: the reaction was initiated at 50° C. for 2 min for the included uracil N-glycosylase to act, followed by reverse transcription at 60° C. for 30 min. After a 5-min denaturation at 95° C., 40 cycles of PCR were carried out using denaturation at 92° C. for 15 s and 1 min annealing/extension at 56° C. for PLAC1, 57° C. for TFPI2 and KISS1, and 58° C. for β-globin.

Statistical analyses were performed using the Sigma Stat 2.03 software (SPSS).

B. Results

Identification of Placental-Specific Genes by High-Density Oligonucleotide Array Analysis of Placental Tissues and Paired Maternal Blood Samples Gene expression profiles of five first-trimester CVS and five term placentas were obtained by microarray analysis of each individual tissue sample. A total of 7226 and 8871 gene transcripts were found to be expressed in the CVS samples and term placentas, respectively. It has been previously reported that circulating DNA in the plasma of normal individuals is predominantly derived from hematopoietic cells (Lui et al., *Clin. Chem.*, 48:421-427, 2002). Thus, it is hypothesized that much of the background maternal nucleic acids in maternal plasma also originate from the hematopoietic compartment. As the ultimate aim of the study was to identify placental-expressed transcripts that are fetal-specific amongst the circulating RNA molecules in maternal plasma, the present inventors further obtained the gene expression profiles of paired maternal whole blood and compared these profiles with those of the corresponding placental tissues using the GeneChip® Microarray Suite 5.0 software (Affymetrix). Fetal-specific placental-expressed transcripts in early pregnancy were identified by selecting transcripts whose expression levels were "increased" in the CVS tissues when compared to the corresponding whole blood samples in all five comparisons. Fetal-specific transcripts of late pregnancy were similarly identified from the term placentas when compared to the paired maternal whole blood samples. After these procedures, transcripts that were highly expressed in both the placental tissues and maternal blood cells were eliminated, resulting in a panel of 1245 and 1743 transcripts identified for the first and third trimesters of pregnancy, respectively. The transcripts on these two panels were then sorted in descending order according to the medians of the five CVS or five term placental tissue microarray expression signals (see Supplementary Tables A and B for the 50 most highly-expressed transcripts for early and late pregnancies, respectively). The two resultant panels consist of candidate transcripts that are potentially detectable in maternal plasma as fetal-specific markers. The strategy used in the identification of such fetal-specific markers is summarized in FIG. 1. The fact that three mRNA transcripts, namely, hPL, βhCG, and CRH, that had been previously found detectable in maternal plasma are present in the list, provides independent validation of this approach. However, as previous studies have not included information on the gene expression levels in the placenta and maternal plasma, these three transcripts were included in further analysis, together with the three novel markers identified in the list, namely, TFPI2, KISS1, and PLAC1. In order to compare the relative gene expression profiles between placental tissues and maternal plasma, transcripts located at different positions on the list were selected. The median microarray expression signal intensities of these six transcripts are summarized in Table 1. The signal intensity of each transcript was first subjected to global scaling of the overall intensities of all arrays to a target intensity value of 500, and the medians of the scaled transcript intensities in the 5 CVS and 5 term placental tissues were determined.

Development of Real-Time QRT-PCR Assays for Measurement of Placental-Expressed Transcripts in Maternal Plasma Six one-step real-time QRT-PCR assays were used. The six selected placental mRNA transcripts were quantified in paired placental tissues and plasma samples from 10 first and 10 third trimester pregnant women by QRT-PCR. The six transcripts were detectable from the placental tissues of all cases. The detectability and the median concentrations of these transcripts in both the first and the third trimester maternal plasma are summarized in Table 1. These results demonstrate that a significant proportion of the selected placental-expressed gene transcripts identified by microarray analysis can indeed be detected in maternal plasma. In general, transcripts with relatively higher median microarray signal intensities are more readily detectable in maternal plasma. On the contrary, a median maternal plasma concentration of zero copy is noted for the least abundant transcripts among the six studied placental-expressed genes, namely, PLAC1 in the first trimester, and hCGβ and PLAC1 in the third trimester. Hence, these data suggest that placental-expressed transcripts can be robustly detected in maternal plasma provided that the expression level exceeds a threshold microarray signal.

Figure 8:
FIG. 8 depicts the clearance of placental mRNA from maternal plasma after delivery. Concentrations of (A) TFPI2 mRNA, (B) KISS1 mRNA, and (C) PLAC1 mRNA in maternal plasma before delivery and at 24 hours after delivery were measured by QRT-PCR. Each line represents one plasma sample obtained from one subject.
Figure 8:
Figure 8:
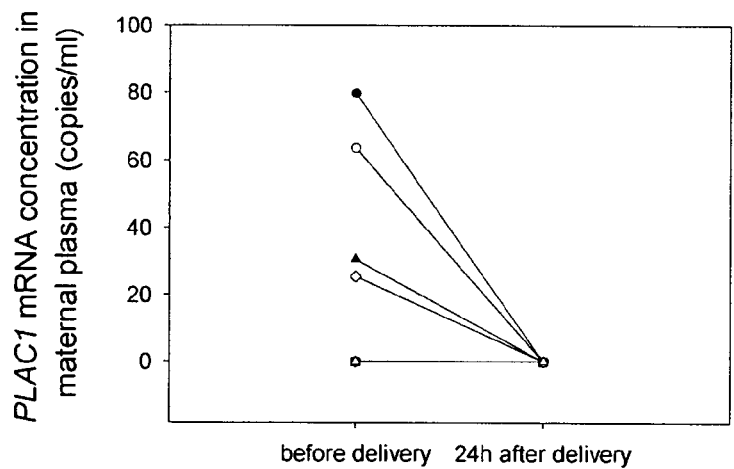

Clearance of the Placental-Expressed Transcripts from Maternal Plasma after Delivery If the studied transcripts were pregnancy-specific, one would expect that they would be cleared from maternal plasma after delivery. As shown in the previous studies (Ng et al., *Proc. Natl. Acad. Sci. USA*, 100:4748-4753, 2003; and Ng et al., *Clin. Chem.*, 49:727-731, 2003), hPL and CRH mRNA molecules were cleared rapidly from maternal plasma after delivery. To investigate the clearance of TFPI2, KISS1, and PLAC1 mRNA from maternal plasma, plasma samples from 10 pregnant women were obtained before and at 24 hours after delivery. In the pre-delivery plasma samples, the median TFPI2 and KISS1 mRNA concentrations were 112 copies/ml and 88 copies/ml, respectively. Both transcripts were not detected in any of the postpartum plasma samples (FIG. 8A and FIG. 8B for TFPI2 and KISS1 mRNA, respectively). For PLAC1 mRNA, the transcript was detected in 4 of the 10 pre-delivery plasma samples, while no signal was detected in any of the postpartum samples (FIG. 8C). As a control, GAPDH mRNA was detected in all pre- and post-delivery plasma samples, with no systematic change in the concentrations (Wilcoxon test, P=0.563).

Figure 9A:
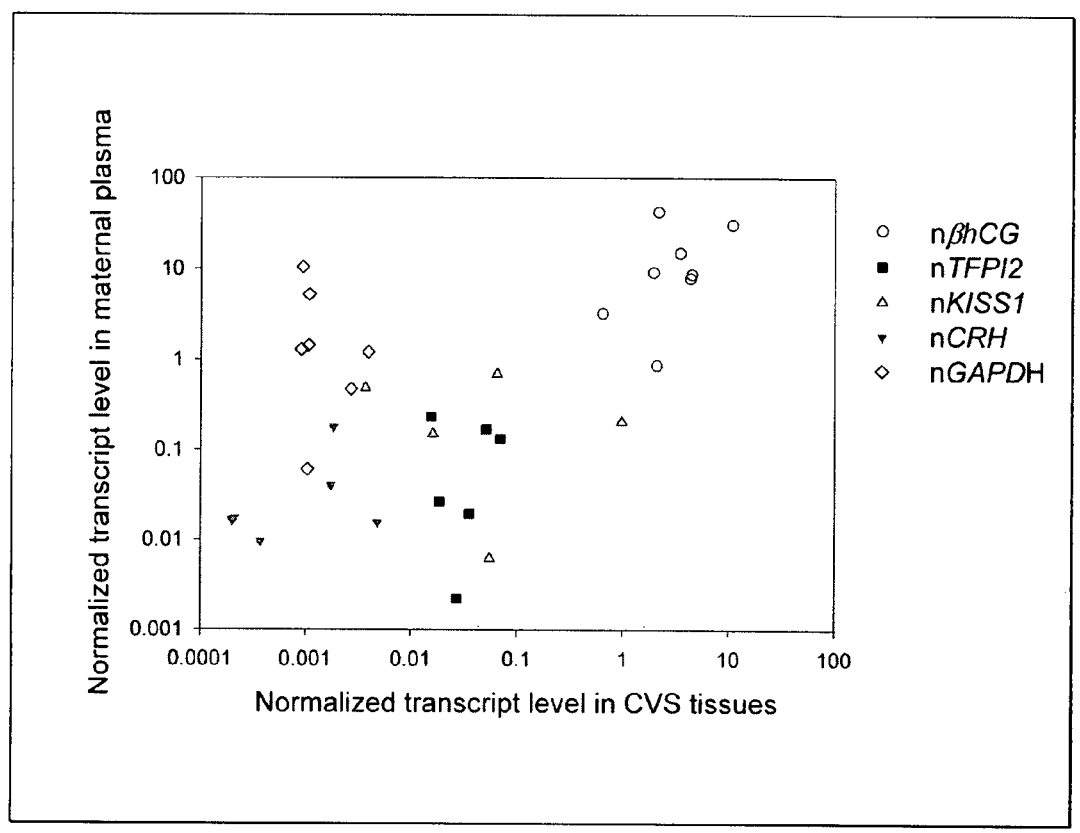
FIG. 9 shows correlation of normalized placental mRNA levels in maternal plasma and placental tissues. (A) Correlation of normalized placental mRNA levels between first-trimester plasma and CVS. (B) Correlation of normalized placental mRNA levels between third-trimester plasma and term placentas. The normalized levels of hCG (nβhCG), TFPI2 (nTFPI2), KISS1 (nKISS1), CRH (nCRH), and PLAC1 (nPLAC1) mRNA in plasma and placental tissues were determined by QRT-PCR and indicated by the respective symbols indicated in the legends. The normalized levels for the non-placental expressed transcripts, GAPDH (nGAPDH) and β-globin (nβ-globin) are also indicated.
Figure 9B:
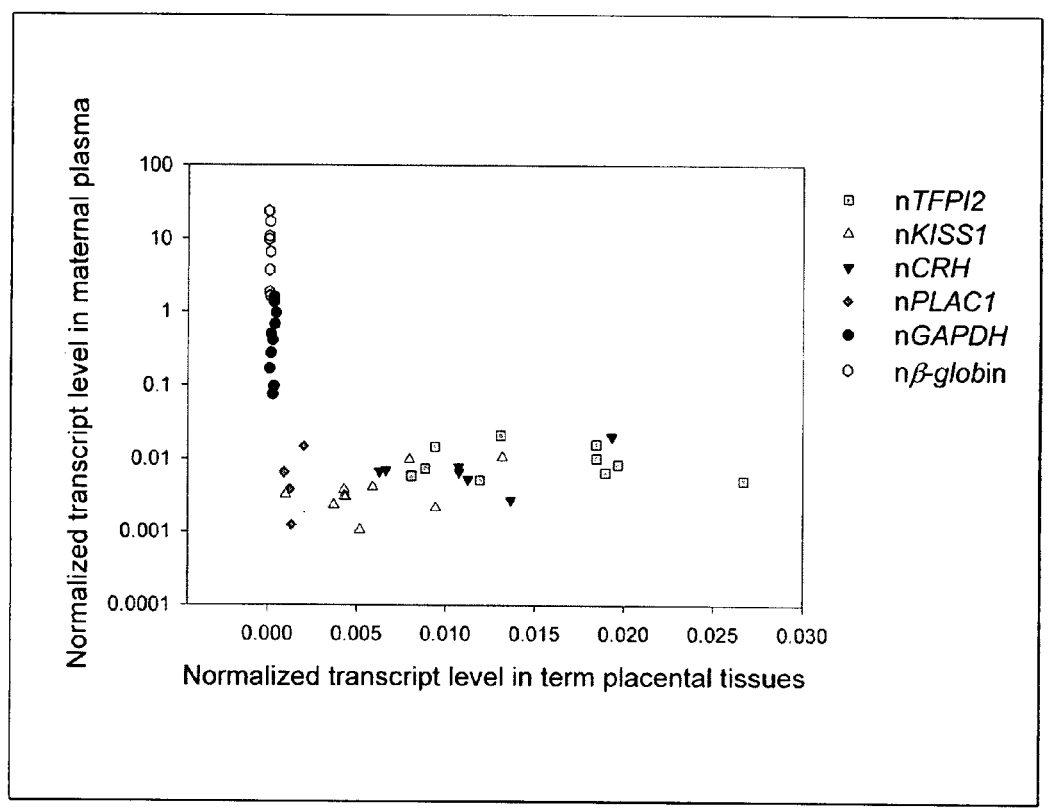

Validation of mRNA Analysis in Maternal Plasma for Non-Invasive Placental Gene Expression Profiling Direct evidence was sought that the measurement of placental transcript levels in maternal plasma would provide an indirect measure of gene expression levels in the placenta. Paired placental and plasma samples from 10 first and 10 third trimester pregnancies were analyzed for hPL, hCGβ, CRH, TFPI2, KISS1, and PLAC1 mRNA by QRT-PCR. It was reasoned that if the levels of these transcripts in maternal plasma were indeed a reflection of their respective levels in the placenta, then a positive correlation should be seen between the relative concentrations of these transcripts in the placenta and in maternal plasma. One practical approach to express the relative levels of these transcripts would be to normalize their levels with respect to a common placental-specific transcript. As hPL mRNA could be detected throughout pregnancy (Ng et al., *Proc. Natl. Acad. Sci. USA*, 100: 4748-4753, 2003), hPL mRNA was chosen as a reference. The normalized level for each transcript was calculated by dividing the transcript level in an individual placenta or plasma sample to the corresponding hPL mRNA level in the same sample. The comparison was only made for transcripts that were detectable in maternal plasma. As PLAC1 and hCGβ were not detectable at all in the current series of first and third trimester maternal plasma samples, respectively, they were not included in the respective analyses. FIGS. 9A and 9B show plots of the normalized transcript levels for hCGβ, CRH, TFPI2, KISS1, and PLAC1 mRNA in the placentas and the paired maternal plasma. A positive correlation was seen between the placental and maternal plasma results for both the first (Spearman correlation analysis, r=0.452, P<0.05) and third (Spearman correlation analysis, r=0.661, P<0.05) trimesters. As a control, two non-placental-specific mRNA transcripts were also analysed: β-globin for the third trimester and GAPDH for both first and third trimester samples. As can be seen in FIGS. 9A and 9B, these non-placental-specific transcripts clearly did not follow the correlative trend exhibited by the placental-specific transcripts. These data suggest that the placental-specific mRNA levels measured from maternal plasma may be used to assess placental gene expression.

C. Conclusion

Figure 7:
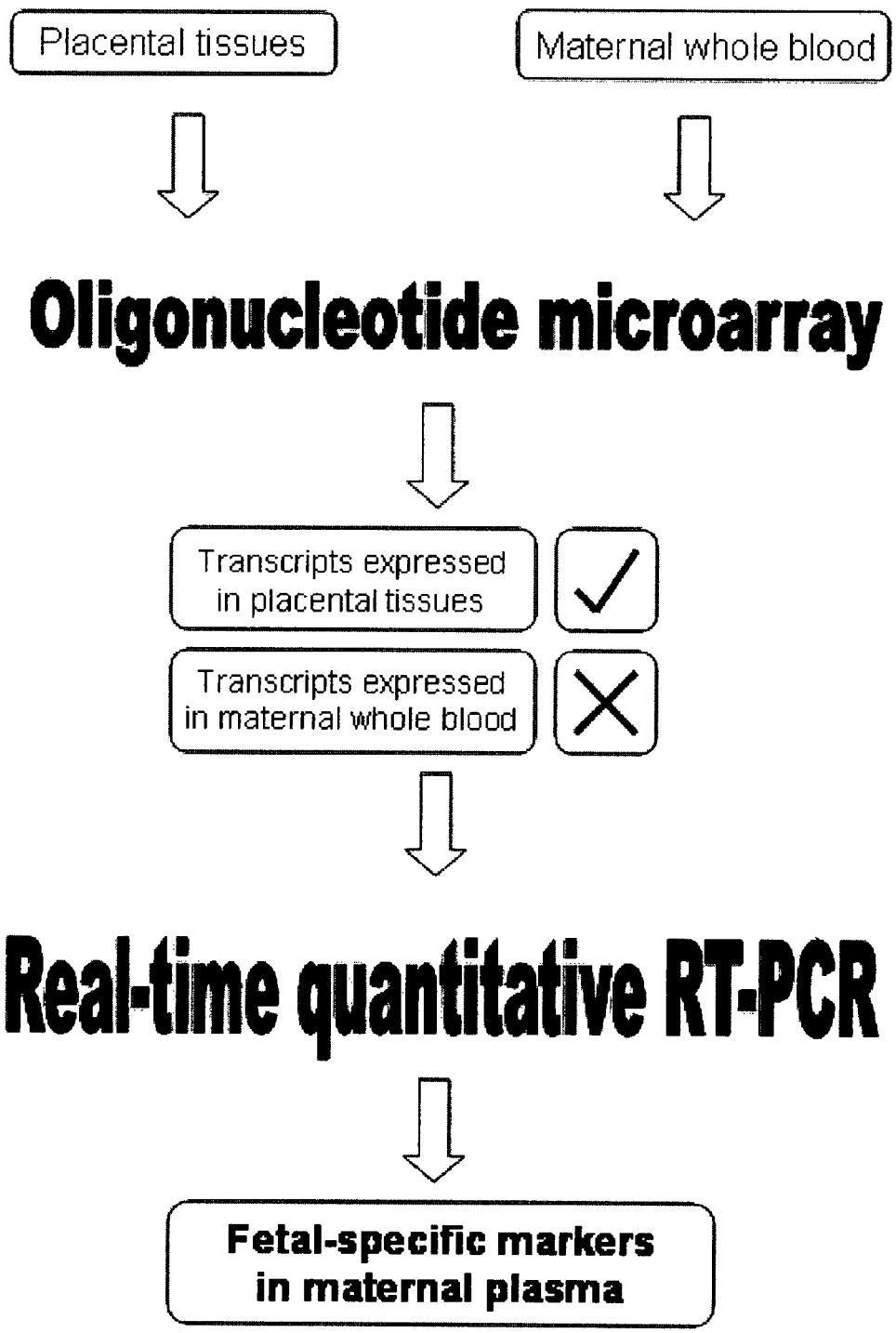
FIG. 7 is an outline of the strategy used for the systematic identification of pregnancy-specific placental-expressed mRNA markers in maternal plasma. Paired placental tissues and maternal whole blood samples are collected and subjected to oligonucleotide microarray analysis. Transcripts with increased expression in the placental tissues relative to whole blood are selected and their detectability in maternal plasma and pregnancy-specificity are evaluated by quantitative reverse transcriptase-PCR (QRT-PCR) on maternal plasma.

A strategy has been developed that allows the systematic identification of a large panel of fetal-specific RNA markers in maternal plasma (FIG. 7). This strategy was devised based on the previous finding that the placenta is an important source of circulating fetal RNA in maternal plasma and the predominant haematological origin of plasma DNA in normal individuals. High-density oligonucleotide microarrays were used to systematically identify a large panel of placental-expressed transcripts and to select the potentially fetal-specific transcripts for maternal plasma detection, with genes expressed by blood cells being discarded as potential targets (Supplementary Tables A and B). Three previously identified plasma placental-specific mRNA markers, coding for hPL, hCGβ, and CRH, were present in the target list and provided independent validation of the transcript selection strategy. In addition, three mRNA markers identified in the list, namely, TFPI2, KISS1, and PLAC1, previously unexplored for non-invasive prenatal monitoring, were also detectable in maternal plasma by QRT-PCR provided that their placental tissue expression level was above a certain threshold. Their rapid clearance from the maternal plasma after delivery confirms the placental-specificity. These findings add further weight to the validity of the strategy used for the identification of fetal-specific transcripts in maternal plasma.

In contrast to the placental-specific mRNA species, no correlation was observed between the plasma and placental normalized mRNA levels of non-placental-specific transcripts, namely, GAPDH and β-globin. Compared with the placental-specific transcripts, relatively more GAPDH and β-globin mRNA was present in the maternal plasma, which might be explained by the contribution of such non-placental-specific transcripts from maternal tissues, e.g., the hematopoietic cells.

In conclusion, it has been demonstrated that circulating placental mRNA in maternal plasma could be used for detection of pregnancy and for non-invasive prenatal gene expression profiling. This study has further outlined a microarray-based approach for rapidly and systematically identifying new placental mRNA markers to be used for this purpose. This development has particular implications for the generation of new markers for the studying and monitoring of conditions known to be associated with placental pathology, such as trisomy 21 and pre-eclampsia. In addition, the findings of this study may have implications beyond pregnancy-related diseases. For example, as tumor-associated mRNA has been detected in the plasma/serum of cancer patients (see, e.g., Lo et al., *Clin. Chem.*, 45:1292-1294, 1999; and Silva et al., *Gut.*, 50:530-534, 2002), a similar approach can be used for rapidly generating new plasma RNA-based tumor markers.

All patents, patent applications, and other publications cited in this application are incorporated by reference in the entirety.

TABLE 1A

Summary of microarray results in CVS samples and QRT-PCR results in first-trimester maternal plasma of the six selected placental transcripts.

| Transcript | median CVS microarray signal | detectability in first-trimester plasma (%) | Median concentration in first-trimester plasma (copies/ml) |
|---|---|---|---|
| βhCG | 31857 | 90 | 4969 |
| hPL | 26503 | 90 | 769 |
| TFPI2 | 24180 | 70 | 38 |
| KISS1 | 19756 | 50 | 18 |
| CRH | 6941 | 70 | 16 |
| PLAC1 | 3020 | 0 | 0 |

TABLE 1B

Summary of microarray results in term placental tissues and QRT-PCR results in third-trimester maternal plasma of the six selected placental transcripts.

| Transcript | median term placentas microarray signal | detectability in third-trimester plasma (%) | median concentration in third-trimester plasma (copies/ml) |
|---|---|---|---|
| hPL | 33972 | 100 | 14707 |
| TFPI2 | 24896 | 100 | 189 |
| CRH | 17077 | 70 | 98 |
| KISS1 | 16033 | 100 | 50 |
| βhCG | 9759 | 0 | 0 |
| PLAC1 | 9755 | 40 | 0 |

Supplementary TABLE A. Microarray detection of the 50 most highly expressed genes in CVS tissues

| Transcript | Probe Set ID | GenBank acc. | Signals (median) |
|---|---|---|---|
| *chorionic gonadotropin, beta polypeptide | 205387_s_at | NM_000737.1 | 31857.3 |
| placental lactogen (v. 4) | 208356_x_at | NM_022642.1 | 28651.4 |
| growth hormone 1 (v. 5) | 208068_x_at | NM_022562.1 | 28500.7 |
| growth hormone 1 (v. 4) | 208069_x_at | NM_022561.1 | 27624.7 |
| chorionic somatomammotropin hormone 2 (v. 1) | 203807_x_at | NM_020991.2 | 27513.2 |
| placental lactogen (clone MGC:14518) | 211739_x_at | BC005921.1 | 27185.9 |
| chorionic somatomammotropin hormone-like 1 (v. 2) | 208294_x_at | NM_022578.1 | 27104.4 |
| *placental lactogen (v. 1) | 202493_x_at | NM_001317.2 | 26503.0 |
| chorionic somatomammotropin hormone 2 (v. 3) | 208342_x_at | NM_022645.1 | 25820.6 |
| placental lactogen (v. 3) | 208357_x_at | NM_022641.1 | 25777.3 |
| chorionic somatomammotropin hormone 2 (v. 4) | 208341_x_at | NM_022646.1 | 25603.1 |
| pregnancy specific beta-1-glycoprotein 1 | 208257_x_at | NM_006905.1 | 25453.4 |
| growth hormone 1 (v. 2) | 206885_x_at | NM_022559.1 | 24834.8 |
| chorionic somatomammotropin hormone-like 1 (v. 1) | 207285_x_at | NM_001318.2 | 24796.9 |
| chorionic somatomammotropin hormone-like 1 (v. 5) | 208293_x_at | NM_022581.1 | 24709.4 |
| pregnancy specific beta-1-glycoprotein 6 | 209738_x_at | M31125.1 | 24370.6 |
| pregnancy specific beta-1-glycoprotein 3 | 203399_x_at | NM_021016.1 | 24262.4 |
| chorionic somatomammotropin hormone-like 1 (v. 4) | 208295_x_at | NM_022580.1 | 24190.7 |
| *tissue factor pathway inhibitor 2 | 209278_s_at | L27624.1 | 24179.9 |
| glycoprotein hormones, alpha polypeptide | 204637_at | NM_000735.2 | 23720.4 |
| growth hormone 1 (v. 3) | 206886_x_at | NM_022560.1 | 23475.7 |
| pregnancy specific beta-1-glycoprotein 3 | 215821_x_at | AB019570.1 | 23095.5 |
| pregnancy specific beta-1-glycoprotein 3 | 211741_x_at | BC005924.1 | 23025.1 |
| growth hormone variant mRNA | 211151_x_at | AF185611.1 | 22792.2 |
| prostate differentiation factor | 221577_x_at | AF003934.1 | 22685.4 |
| growth hormone 1 (v. 1) | 205840_x_at | NM_000515.2 | 22446.6 |
| chorionic somatomammotropin hormone-like 1 (v. 3) | 205958_x_at | NM_022579.1 | 22097.6 |
| pregnancy specific beta-1-glycoprotein 4 | 208191_x_at | NM_002780.1 | 20730.7 |
| pregnancy specific beta-1-glycoprotein 2 | 208134_x_at | NM_031246.1 | 20233.5 |
| pregnancy specific beta-1-glycoprotein 9 | 209594_x_at | M34421.1 | 19939.4 |
| *KiSS-1 metastasis-suppressor | 205563_at | NM_002256.1 | 19755.8 |
| placental lactogen (v. 2) | 206475_x_at | NM_022640.1 | 19367.1 |
| pregnancy specific beta-1-glycoprotein 5 | 204830_x_at | NM_002781.1 | 19182.6 |
| growth hormone 2 | 211508_s_at | AF006060.1 | 18019.7 |
| S100 calcium binding protein P | 204351_at | NM_005980.1 | 17970.2 |
| pregnancy specific beta-1-glycoprotein 6 | 208106_x_at | NM_002782.3 | 17566.8 |
| chorionic somatomammotropin hormone 2 (v. 2) | 207770_x_at | NM_022644.1 | 17244.2 |
| CD63 antigen (melanoma 1 antigen) | 200663_at | NM_001780.1 | 17061.2 |
| delta-like 1 homolog (Drosophila) | 209560_s_at | U15979.1 | 16415.0 |
| fibronectin 1 | 210495_x_at | AF130095.1 | 16046.9 |
| Homo sapiens cDNA: FLJ22066 fis, clone HEP10611 | 202409_at | X07868 | 16024.8 |
| fibronectin 1 | 216442_x_at | AK026737.1 | 15834.1 |
| ribosomal protein L31 | 200963_x_at | NM_000993.1 | 15252.6 |
| a disintegrin and metalloproteinase domain 12 (v. 2) | 204943_at | NM_021641.1 | 15007.3 |
| collagen, type III, alpha 1 (clone HEMBA1001071) | 215076_s_at | AU144167 | 14999.1 |
| pregnancy specific beta-1-glycoprotein 9 | 207733_x_at | NM_002784.1 | 14819.7 |
| secreted phosphoprotein 1 | 209875_s_at | M83248.1 | 14665.3 |
| Epstein-Barr virus induced gene 3 | 219424_at | NM_005755.1 | 14617.0 |

Supplementary TABLE A. Microarray detection of the 50 most highly expressed genes in CVS tissues

| Transcript | Probe Set ID | GenBank acc. | Signals (median) |
|---|---|---|---|
| collagen, type III, alpha 1 | 201852_x_at | AI813758 | 14494.7 |
| fibronectin 1 | 211719_x_at | BC005858.1 | 14157.1 | v, transcripts variant; *transcripts selected for QRT-PCR study
*cortocotropin releasing hormone is located at position 156 on this list
*placenta-specific 1 is located at position 412 on this list Supplementary TABLE B. Microarray detection of the 50 most highly expressed genes in term placental tissues

| Transcript | Probe Set ID | GenBank acc. | Signals (median) |
|---|---|---|---|
| chorionic somatomammotropin hormone 2 (v. 1) | 203807_x_at | NM_020991.2 | 35768.0 |
| placental lactogen (clone MGC:1451) | 211739_x_at | BC005921.1 | 35732.4 |
| placental lactogen (v. 4) | 208356_x_at | NM_022642.1 | 35099.3 |
| *placental lactogen (v. 1) | 202493_x_at | NM_001317.2 | 33972.4 |
| growth hormone 1 (v. 5) | 208068_x_at | NM_022562.1 | 33265.8 |
| chorionic somatomammotropin hormone-like 1 (v. 2) | 208294_x_at | NM_022578.1 | 32947.1 |
| placental lactogen (v. 3) | 208357_x_at | NM_022641.1 | 32826.0 |
| chorionic somatomammotropin hormone 2 (v. 4) | 208341_x_at | NM_022646.1 | 32231.7 |
| chorionic somatomammotropin hormone 2 (v. 3) | 208342_x_at | NM_022645.1 | 31623.2 |
| growth hormone 1 (v. 4) | 208069_x_at | NM_022561.1 | 30524.9 |
| chorionic somatomammotropin hormone-like 1 (v. 4) | 208295_x_at | NM_022580.1 | 30349.2 |
| chorionic somatomammotropin hormone-like 1 (v. 5) | 208293_x_at | NM_022581.1 | 30076.9 |
| growth hormone 1 (v. 2) | 206885_x_at | NM_022559.1 | 29888.7 |
| pregnancy specific beta-1-glycoprotein 9 | 209594_x_at | M34421.1 | 29462.1 |
| growth hormone 1 (v. 1) | 205840_x_at | NM_000515.2 | 28856.8 |
| pregnancy specific beta-1-glycoprotein 6 | 209738_x_at | M31125.1 | 28736.3 |
| chorionic somatomammotropin hormone-like 1, (v. 1) | 207285_x_at | NM_001318.2 | 28532.6 |
| growth hormone 1 (v. 3) | 206886_x_at | NM_022560.1 | 27576.2 |
| pregnancy specific beta-1-glycoprotein 1 | 208257_x_at | NM_006905.1 | 26521.2 |
| pregnancy specific beta-1-glycoprotein 3 | 211741_x_at | BC005924.1 | 26306.1 |
| growth hormone variant (GHV) mRNA | 211151_x_at | AF185611.1 | 26127.2 |
| pregnancy specific beta-1-glycoprotein 3 | 203399_x_at | NM_021016.1 | 25987.8 |
| placental lactogen (v. 2) | 206475_x_at | NM_022640.1 | 25873.3 |
| chorionic somatomammotropin hormone-like 1 (v. 3) | 205958_x_at | NM_022579.1 | 25597.7 |
| a disintegrin and metalloproteinase domain 12 (v. 2) | 204943_at | NM_021641.1 | 25592.8 |
| pregnancy specific beta-1-glycoprotein 3 | 215821_x_at | AB019570.1 | 24944.4 |
| *tissue factor pathway inhibitor 2 | 209278_s_at | L27624.1 | 24896.4 |
| glycoprotein hormones, alpha polypeptide | 204637_at | NM_000735.2 | 24831.5 |
| pregnancy specific beta-1-glycoprotein 5 | 204830_x_at | NM_002781.1 | 23928.8 |
| pregnancy specific beta-1-glycoprotein 2 | 208134_x_at | NM_031246.1 | 23786.0 |
| pregnancy specific beta-1-glycoprotein 4 | 208191_x_at | NM_002780.1 | 23475.2 |
| chorionic somatomammotropin hormone 2 (v. 2) | 207770_x_at | NM_022644.1 | 22227.9 |
| pregnancy specific beta-1-glycoprotein 9 | 207733_x_at | NM_002784.1 | 22088.4 |
| prostate differentiation factor | 221577_x_at | AF003934.1 | 20335.8 |
| cytochrome P450, subfamily XIX | 203475_at | NM_000103.1 | 20147.5 |
| delta-like 1 homolog (*Drosophila*) | 209560_s_at | U15979.1 | 19268.5 |
| pregnancy specific beta-1-glycoprotein 6 | 208106_x_at | NM_002782.3 | 19225.4 |
| *Homo sapiens* cDNA FLJ39399 fis, clone PLACE6011041 | 213332_at | AL031290 | 18524.9 |
| S100 calcium binding protein P | 204351_at | NM_005980.1 | 18480.2 |
| *Homo sapiens* cDNA: FLJ22066 fis, clone HEP10611 | 202409_at | X07868 | 17518.8 |
| CD59 antigen p18-20 | 200983_x_at | NM_000611.1 | 17295.0 |
| *corticotropin releasing hormone | 205630_at | NM_000756.1 | 17076.6 |
| a disintegrin and metalloproteinase domain 12 (v. 1) | 202952_s_at | NM_003474.2 | 16992.6 |
| growth hormone 2 | 211508_s_at | AF006060.1 | 16251.8 |
| pregnancy specific beta-1-glycoprotein 7 | 205602_x_at | NM_002783.1 | 16174.5 |
| *KiSS-1 metastasis-suppressor | 205563_at | NM_002256.1 | 16033.3 |
| dipeptidylpeptidase 7 | 200878_at | AF052094.1 | 15227.5 |
| hydroxy-delta-5-steroid dehydrogenase, 3 beta- and steroid delta-isomerase 1 | 204515_at | NM_000862.1 | 14394.6 |
| *Homo sapiens* mRNA full length insert cDNA clone EUROIMAGE 1695532 | 201981_at | AA148534 | 14277.2 |
| fibulin 1 | 201787_at | NM_001996.1 | 14020.6 | v, transcripts variant; *transcripts selected for QRT-PCR study
*placenta-specific-1 is located at position 82 on this list
*chorionic gonadotropin, beta polypeptide is located at position 84 on this list

What is claimed is:

1. A method for detecting pregnancy in a woman, the method comprising the steps of:
   (i) quantitatively determining the amount of KiSS-1 metastasis-suppressor (KISS1) mRNA in the woman's blood; and
   (ii) comparing the amount of KISS1 mRNA from step (i) to a standard control representing the amount of KISS1 mRNA in the blood of an average non-pregnant woman, wherein an increase in the amount of KISS1 mRNA from step (i) as compared to the standard control indicates pregnancy.

2. The method of claim 1, wherein step (i) is performed by reverse transcriptase polymerase chain reaction (RT-PCR).

3. The method of claim 1, wherein step (i) is performed by a polynucleotide hybridization method.

4. The method of claim 1, wherein step (i) is performed by mass spectrometry.

5. The method of claim 1, wherein the woman's blood is rendered acellular prior to step (i).

6. The method of claim 1, wherein the woman's blood is plasma.

7. The method of claim 1, wherein the woman's blood is serum.

8. The method of claim 1, wherein the increase in the amount of KISS1 mRNA from the standard control is more than 2-fold.

* * * * *

SEQUENCE LISTING

<160> NUMBER OF SEQ ID NOS: 28

<210> SEQ ID NO 1
<211> LENGTH: 19
<212> TYPE: DNA
<213> ORGANISM: Artificial Sequence
<220> FEATURE:
<223> OTHER INFORMATION: one-step real-time quantitative RT-PCR
      corticotropin releasing hormone (CRH) forward
      primer

<400> SEQUENCE: 1
gcctcccatc tccctggat                                                  19

<210> SEQ ID NO 2
<211> LENGTH: 22
<212> TYPE: DNA
<213> ORGANISM: Artificial Sequence
<220> FEATURE:
<223> OTHER INFORMATION: one-step real-time quantitative RT-PCR
      corticotropin releasing hormone (CRH) reverse
      primer

<400> SEQUENCE: 2
tgtgagcttg ctgtgctaac tg                                              22

<210> SEQ ID NO 3
<211> LENGTH: 25
<212> TYPE: DNA
<213> ORGANISM: Artificial Sequence
<220> FEATURE:
<223> OTHER INFORMATION: corticotropin releasing hormone (CRH)
      dual-labelled fluorescent probe
<220> FEATURE:
<221> NAME/KEY: modified_base
<222> LOCATION: (1)...(1)
<223> OTHER INFORMATION: n = 6-carboxyfluorescein (FAM) modified t
<220> FEATURE:
<221> NAME/KEY: modified_base
<222> LOCATION: (25)...(25)
<223> OTHER INFORMATION: n = 6-carboxytetramethylrhodamine (TAMRA)
      modified c

<400> SEQUENCE: 3
ncctccggga agtcttggaa atggn                                           25

<210> SEQ ID NO 4
<211> LENGTH: 95
<212> TYPE: DNA
<213> ORGANISM: Artificial Sequence
<220> FEATURE:
<223> OTHER INFORMATION: high performance liquid chromatography-purified
      single stranded synthetic DNA oligonucleotide
      corticotropin releasing hormone (CRH) amplicon for
      CRH calibrations

<400> SEQUENCE: 4
ggagcctccc atctccctgg atctcacctt ccacctcctc cgggaagtct tggaaatggc     60
cagggccgag cagttagcac agcaagctca cagca                                95

<210> SEQ ID NO 5
<211> LENGTH: 21
<212> TYPE: DNA
<213> ORGANISM: Artificial Sequence
<220> FEATURE:
<223> OTHER INFORMATION: one-step real-time quantitative RT-PCR
      intron-spanning human placental lactogen (hPL)

```
            sense primer

<400> SEQUENCE: 5
catgactccc agacctcctt c                                              21

<210> SEQ ID NO 6
<211> LENGTH: 20
<212> TYPE: DNA
<213> ORGANISM: Artificial Sequence
<220> FEATURE:
<223> OTHER INFORMATION: one-step real-time quantitative RT-PCR
      intron-spanning human placental lactogen (hPL)
      antisense primer

<400> SEQUENCE: 6
tgcggagcag ctctagattg                                                20

<210> SEQ ID NO 7
<211> LENGTH: 25
<212> TYPE: DNA
<213> ORGANISM: Artificial Sequence
<220> FEATURE:
<223> OTHER INFORMATION: human placental lactogen (hPL) dual-labelled
      fluorescence probe
<220> FEATURE:
<221> NAME/KEY: modified_base
<222> LOCATION: (1)...(1)
<223> OTHER INFORMATION: n = 6-carboxyfluorescein (FAM) modified t
<220> FEATURE:
<221> NAME/KEY: modified_base
<222> LOCATION: (25)...(25)
<223> OTHER INFORMATION: n = 6-carboxytetramethylrhodamine (TAMRA)
      modified g

<400> SEQUENCE: 7
ntctgttgcg tttcctccat gttgn                                          25

<210> SEQ ID NO 8
<211> LENGTH: 20
<212> TYPE: DNA
<213> ORGANISM: Artificial Sequence
<220> FEATURE:
<223> OTHER INFORMATION: one-step real-time quantitative RT-PCR
      intron-spanning human chorionic gonadotropin beta
      subunit (hCG-beta) sense primer

<400> SEQUENCE: 8
ctactgcccc accatgaccc                                                20

<210> SEQ ID NO 9
<211> LENGTH: 19
<212> TYPE: DNA
<213> ORGANISM: Artificial Sequence
<220> FEATURE:
<223> OTHER INFORMATION: one-step real-time quantitative RT-PCR
      intron-spanning human chorionic gonadotropin beta
      subunit (hCG-beta) antisense primer

<400> SEQUENCE: 9
tggactcgaa gcgcacatc                                                 19

<210> SEQ ID NO 10
<211> LENGTH: 25
<212> TYPE: DNA
<213> ORGANISM: Artificial Sequence
<220> FEATURE:
<223> OTHER INFORMATION: human chorionic gonadotropin beta subunit
      (hCG-beta) dual-labelled fluorescent probe
<220> FEATURE:
```

<221> NAME/KEY: modified_base
<222> LOCATION: (1)...(1)
<223> OTHER INFORMATION: n = 6-carboxyfluorescein (FAM) modified c
<220> FEATURE:
<221> NAME/KEY: modified_base
<222> LOCATION: (25)...(25)
<223> OTHER INFORMATION: n = 6-carboxytetramethylrhodamine (TAMRA) modified c

<400> SEQUENCE: 10
nctgcctcag gtggtgtgca actan                                      25

<210> SEQ ID NO 11
<211> LENGTH: 98
<212> TYPE: DNA
<213> ORGANISM: Artificial Sequence
<220> FEATURE:
<223> OTHER INFORMATION: high performance liquid chromatography-purified
      single stranded synthetic DNA oligonucleotide
      human placental lactogen (hPL) amplicon for hPL
      calibrations

<400> SEQUENCE: 11
tgcggagcag ctctagattg gatttctgtt gcgtttcctc catgttggag ggtgtcggaa    60
tagagtctga gaagcagaag gaggtctggg agtcatgc                          98

<210> SEQ ID NO 12
<211> LENGTH: 96
<212> TYPE: DNA
<213> ORGANISM: Artificial Sequence
<220> FEATURE:
<223> OTHER INFORMATION: high performance liquid chromatography-purified
      single stranded synthetic DNA oligonucleotide
      human chorionic gonadotropin beta subunit
      (hCG-beta) amplicon for hCG-beta calibrations

<400> SEQUENCE: 12
gatggactcg aagcgcacat cgcggtagtt gcacaccacc tgaggcaggg ccggcaggac    60
cccctgcagc acgcgggtca tggtggggca gtagcc                            96

<210> SEQ ID NO 13
<211> LENGTH: 23
<212> TYPE: DNA
<213> ORGANISM: Artificial Sequence
<220> FEATURE:
<223> OTHER INFORMATION: one-step real-time quantitative RT-PCR tissue
      factor pathway inhibitor 2 (TFPI2) sense primer

<400> SEQUENCE: 13
acaaatttct acacctggga ggc                                         23

<210> SEQ ID NO 14
<211> LENGTH: 21
<212> TYPE: DNA
<213> ORGANISM: Artificial Sequence
<220> FEATURE:
<223> OTHER INFORMATION: one-step real-time quantitative RT-PCR tissue
      factor pathway inhibitor 2 (TFPI2) antisense
      primer

<400> SEQUENCE: 14
cggcaaactt tgggaacttt t                                           21

<210> SEQ ID NO 15
<211> LENGTH: 22
<212> TYPE: DNA
<213> ORGANISM: Artificial Sequence

```
<220> FEATURE:
<223> OTHER INFORMATION: tissue factor pathway inhibitor 2 (TFPI2)
      dual-labelled fluorescent probe
<220> FEATURE:
<221> NAME/KEY: modified_base
<222> LOCATION: (1)...(1)
<223> OTHER INFORMATION: n = 6-carboxyfluorescein (FAM) modified t
<220> FEATURE:
<221> NAME/KEY: modified_base
<222> LOCATION: (22)...(22)
<223> OTHER INFORMATION: n = 6-carboxytetramethylrhodamine (TAMRA)
      modified a

<400> SEQUENCE: 15
ngcgacgatg cttgctggag gn                                               22

<210> SEQ ID NO 16
<211> LENGTH: 17
<212> TYPE: DNA
<213> ORGANISM: Artificial Sequence
<220> FEATURE:
<223> OTHER INFORMATION: one-step real-time quantitative RT-PCR KiSS1
      metastasis-suppressor (KISS1) sense primer

<400> SEQUENCE: 16
gcccaggcca ggactga                                                     17

<210> SEQ ID NO 17
<211> LENGTH: 23
<212> TYPE: DNA
<213> ORGANISM: Artificial Sequence
<220> FEATURE:
<223> OTHER INFORMATION: one-step real-time quantitative RT-PCR KiSS1
      metastasis-suppressor (KISS1) antisense primer

<400> SEQUENCE: 17
gccaagaaac cagtgagttc atc                                              23

<210> SEQ ID NO 18
<211> LENGTH: 30
<212> TYPE: DNA
<213> ORGANISM: Artificial Sequence
<220> FEATURE:
<223> OTHER INFORMATION: KiSS1 metastasis-suppressor (KISS1)
      dual-labelled fluorescent probe
<220> FEATURE:
<221> NAME/KEY: modified_base
<222> LOCATION: (1)...(1)
<223> OTHER INFORMATION: n = 6-carboxyfluorescein (FAM) modified c
<220> FEATURE:
<221> NAME/KEY: modified_base
<222> LOCATION: (30)...(30)
<223> OTHER INFORMATION: n = 6-carboxytetramethylrhodamine (TAMRA)
      modified c

<400> SEQUENCE: 18
nctcaaggca cttctaggac ctggctcttn                                       30

<210> SEQ ID NO 19
<211> LENGTH: 20
<212> TYPE: DNA
<213> ORGANISM: Artificial Sequence
<220> FEATURE:
<223> OTHER INFORMATION: one-step real-time quantitative RT-PCR
      placenta-specific 1 (PLAC1) sense primer

<400> SEQUENCE: 19
attatcccca gctgccagaa                                                  20
```

```
<210> SEQ ID NO 20
<211> LENGTH: 23
<212> TYPE: DNA
<213> ORGANISM: Artificial Sequence
<220> FEATURE:
<223> OTHER INFORMATION: one-step real-time quantitative RT-PCR
      placenta-specific 1 (PLAC1) antisense primer

<400> SEQUENCE: 20
gcagccaatc agataatgaa cca                                             23

<210> SEQ ID NO 21
<211> LENGTH: 27
<212> TYPE: DNA
<213> ORGANISM: Artificial Sequence
<220> FEATURE:
<223> OTHER INFORMATION: placenta-specific 1 (PLAC1) dual-labelled
      fluorescent probe
<220> FEATURE:
<221> NAME/KEY: modified_base
<222> LOCATION: (1)...(1)
<223> OTHER INFORMATION: n = 6-carboxyfluorescein (FAM) modified a
<220> FEATURE:
<221> NAME/KEY: modified_base
<222> LOCATION: (27)...(27)
<223> OTHER INFORMATION: n = 6-carboxytetramethylrhodamine (TAMRA)
      modified g

<400> SEQUENCE: 21
nagaaatcct cactggacgg cttcctn                                         27

<210> SEQ ID NO 22
<211> LENGTH: 20
<212> TYPE: DNA
<213> ORGANISM: Artificial Sequence
<220> FEATURE:
<223> OTHER INFORMATION: one-step real-time quantitative RT-PCR
      beta-globin sense primer

<400> SEQUENCE: 22
gctgcactgt gacaagctgc                                                 20

<210> SEQ ID NO 23
<211> LENGTH: 20
<212> TYPE: DNA
<213> ORGANISM: Artificial Sequence
<220> FEATURE:
<223> OTHER INFORMATION: one-step real-time quantitative RT-PCR
      beta-globin antisense primer

<400> SEQUENCE: 23
gcacacagac cagcacgttg                                                 20

<210> SEQ ID NO 24
<211> LENGTH: 25
<212> TYPE: DNA
<213> ORGANISM: Artificial Sequence
<220> FEATURE:
<223> OTHER INFORMATION: beta-globin dual-labelled fluorescence probe
<220> FEATURE:
<221> NAME/KEY: modified_base
<222> LOCATION: (1)...(1)
<223> OTHER INFORMATION: n = 6-carboxyfluorescein (FAM) modified c
<220> FEATURE:
<221> NAME/KEY: modified_base
<222> LOCATION: (25)...(25)
<223> OTHER INFORMATION: n = 6-carboxytetramethylrhodamine (TAMRA)
      modified c

<400> SEQUENCE: 24
```
ngtggatcct gagaacttca ggctn    25

<210> SEQ ID NO 25
<211> LENGTH: 79
<212> TYPE: DNA
<213> ORGANISM: Artificial Sequence
<220> FEATURE:
<223> OTHER INFORMATION: high performance liquid chromatography-purified
      single stranded synthetic DNA oligonucleotide
      tissue factor pathway inhibitor 2 (TFPI2) amplicon
      for TFPI2 calibrations

<400> SEQUENCE: 25
cgccaacaat ttctacacct gggaggcttg cgacgatgct tgctggagga tagaaaagt    60 tcccaaagtt tgccggctg    79

<210> SEQ ID NO 26
<211> LENGTH: 87
<212> TYPE: DNA
<213> ORGANISM: Artificial Sequence
<220> FEATURE:
<223> OTHER INFORMATION: high performance liquid chromatography-purified
      single stranded synthetic DNA oligonucleotide
      KiSS1 metastasis-suppressor (KISS1) amplicon for
      KISS1 calibrations

<400> SEQUENCE: 26
ctgcccaggc caggactgag gcaagcctca aggcacttct aggacctggc tcttctcacc    60
aagatgaact cactggtttc ttggcag    87

<210> SEQ ID NO 27
<211> LENGTH: 85
<212> TYPE: DNA
<213> ORGANISM: Artificial Sequence
<220> FEATURE:
<223> OTHER INFORMATION: high performance liquid chromatography-purified
      single stranded synthetic DNA oligonucleotide
      placenta-specific 1 (PLAC1) amplicon for PLAC1
      calibrations

<400> SEQUENCE: 27
acaaattatc cccagctgcc agaagaagaa atcctcactg gacggcttcc tgtttcctgt    60
ggttcattat ctgattggct gcagg    85

<210> SEQ ID NO 28
<211> LENGTH: 77
<212> TYPE: DNA
<213> ORGANISM: Artificial Sequence
<220> FEATURE:
<223> OTHER INFORMATION: high performance liquid chromatography-purified
      single stranded synthetic DNA oligonucleotide
      beta-globin amplicon for beta-globin calibrations

<400> SEQUENCE: 28
tgagctgcac tgtgacaagc tgcacgtgga tcctgagaac ttcaggctcc tgggcaacgt    60
gctggtctgt gtgctgg    77